(12) United States Patent
Barenholz et al.

(10) Patent No.: US 7,771,711 B2
(45) Date of Patent: Aug. 10, 2010

(54) SPHINGOLIPIDS' POLYALKYLAMINES CONJUGATES

(75) Inventors: Yechezkel Barenholz, Jerusalem (IL); Dmitri Simberg, Jerusalem (IL); Elimelech Rochlin, Jerusalem (IL)

(73) Assignees: Yissum Research Development Company of The Hebrew University of Jerusalem, Jerusalem (IL); Biolab Ltd., Jerusalem (IL)

( * ) Notice: Subject to any disclaimer, the term of this patent is extended or adjusted under 35 U.S.C. 154(b) by 249 days.

(21) Appl. No.: 10/561,394

(22) PCT Filed: Jun. 17, 2004

(86) PCT No.: PCT/IL2004/000536

§ 371 (c)(1),
(2), (4) Date: Mar. 21, 2007

(87) PCT Pub. No.: WO2004/110980

PCT Pub. Date: Dec. 23, 2004

(65) Prior Publication Data

US 2008/0112917 A1 May 15, 2008

Related U.S. Application Data

(60) Provisional application No. 60/545,505, filed on Feb. 19, 2004, provisional application No. 60/537,553, filed on Jan. 21, 2004, provisional application No. 60/505,638, filed on Sep. 25, 2003, provisional application No. 60/479,185, filed on Jun. 18, 2003.

(51) Int. Cl.
*A61K 31/74* (2006.01)
(52) U.S. Cl. ............... 424/78.27; 514/78; 525/540; 554/78
(58) Field of Classification Search ................ 554/84; 564/281; 568/700
See application file for complete search history.

(56) References Cited

U.S. PATENT DOCUMENTS

| | | | |
|---|---|---|---|
| 4,897,355 | A | 1/1990 | Eppstein et al. |
| 5,171,678 | A | 12/1992 | Behr et al. |
| 5,334,761 | A | 8/1994 | Gebeyehu et al. |
| 5,659,011 | A | 8/1997 | Waldmann |
| 5,674,908 | A | 10/1997 | Haces et al. |
| 5,783,565 | A | 7/1998 | Lee et al. |
| 6,075,012 | A | 6/2000 | Gebeyehu et al. |
| 6,281,371 | B1 | 8/2001 | Klosel et al. |
| 2001/0048939 | A1 | 12/2001 | Erbacher et al. |

FOREIGN PATENT DOCUMENTS

| | | |
|---|---|---|
| EP | 0 394 111 A1 | 10/1990 |
| WO | WO 98/05678 A2 | 2/1998 |
| WO | WO 99/02190 A | 1/1999 |
| WO | WO 01038295 * | 5/2001 |
| WO | WO 03/066068 A1 | 8/2003 |

OTHER PUBLICATIONS

International Search Report mailed Oct. 22, 2004 (corresponding PCT Appln. No. PCT/IL2004/000533).
International Search Report mailed Nov. 16, 2004 (corresponding PCT Appln. No. PCT/IL2004/000534).
International Search Report mailed Oct. 22, 2004 (corresponding PCT Appln. No. PCT/IL2004/000536).
Australian Patent Office Examination Report mailed Jun. 30, 2006 (corresponding Singapore Application No. SG200508078-3).
F. Brunel et al., "Cationic lipid DC-Chol induces an improved and balanced immunity able to overcome the unresponsiveness to the hepatitis B vaccine", *Vaccine* vol. 17, pp. 2192-2203, 1999.
K. Ewert et al., "Efficient Synthesis and Cell-Transfection Properties of a New Multivalent Cationic Lipid for Nonviral Gene Delivery", *J. Med. Chem.* vol. 45, pp. 5023-5029, 2002.
P. L. Felgner et al., "Lipofection: A highly efficient, lipid-mediated DNA-transfection procedure" *Proc. Natl. Acad. Sci. USA.*, vol. 84, pp. 7413-7417, Nov. 1987.
X. Gao et al., "A Novel Cationic Liposome Reagent for Efficient Transfection of Mammalian Cells", *Biochim. Biophys. Acta.* vol. 179, pp. 280-285, 1999.
B. Guy et al., "Design, characterization and preclinical efficacy of a cationic lipid adjuvant for influenza split vaccine", *Vaccine* vol. 19, pp. 1794-1805, 2001.
M. A. Ilies et al., "Recent developments in cationic lipid-mediated gene delivery and gene therapy", *Expert. Opin. Ther. Patents.*, vol. 11, No. 11, pp. 1729-1752, 2001.
K. M. Lima et al., "Comparison of different delivery systems of vaccination for the induction of protection against tuberculosis in mice", *Vaccine* vol. 19, pp. 3518-3525, 2001.
A. D. Miller, "Cationic Liposomes for Gene Therapy", *Chem. Int.* Ed. Eng., vol. 37, pp. 1768-1785, 1987.
T. Nakanishi et al., "Positively charged liposome functions as an efficient immunoadjuvant in inducing cell-mediated immune response to soluble proteins", *J. Controlled Release.* vol. 61, pp. 233-240, 1999.
M. Saminathan et al., "Ionic and Structural Specificity Effects of Natural and Synthetic Polyamines on the Aggregation and Resolubilization of Single-, Double-, and Triple-stranded DNA", *Biochemistry*, vol. 38, pp. 3821-3830, 1999.

\* cited by examiner

*Primary Examiner*—Sikarl A Witherspoon
*Assistant Examiner*—Chukwuma O Nwaonicha
(74) *Attorney, Agent, or Firm*—Browdy and Neimark, PLLC

(57) ABSTRACT

The present invention concerns novel sphingolipid-polyalkylamines conjugates, a process for their preparation and pharmaceutical compositions comprising the same. In particular, the present invention concerns ceramide based polyalkylamine conjugates and its use as a capturing agent. A preferred ceramide polyalkylamine conjugate is a ceramide-spermine conjugate, more preferably, N-palmitoyl D-erythro sphingosyl-1-carbamoyl spermine.

24 Claims, 14 Drawing Sheets

SPHINGOLIPIDS' POLYALKYLAMINES CONJUGATES

FIELD OF THE INVENTION

The present invention concerns novel sphingolipids' polyalkylamines conjugates and their use, inter alia, for transfection.

LIST OF PRIOR ART

The following is a list of prior art which is considered to be pertinent for describing the state of the art in the field of the invention.

U.S. Pat. No. 6,075,012: "Reagents for intracellular delivery of macromolecules";

U.S. Pat. No. 5,783,565: "Cationic amphiphiles containing spermine or spermidine cationic group for intracellular delivery of therapeutic molecules";

U.S. Pat. No. 5,334,761: "Cationic lipids";

US 2001/048939: "Cationic reagents of transfection";

U.S. Pat. No. 5,659,011: "Agents having high nitrogen content and high cationic charge based on dicyanimide dicyandiamide or guanidine and inorganic ammonium salts";

U.S. Pat. No. 5,674,908: "Highly packed polycationic ammonium, sulfonium and phosphonium lipids";

WO 98/05678: "Novel cationic amphiphilic lipids for liposomal gene transfer";

U.S. Pat. No. 6,281,371: "Lipopolyamines, and the preparation and use thereof";

Marc Antoniu Ilies & Alexandru T. Balaban, Expert Opin. Ther. Patents. 11(11):1729-1752 (2001);

Miller A D. Chem. Int. Ed. Eng. 37:1768-1785 (1998).

BACKGROUND OF THE INVENTION

Many natural biological molecules and their analogues, including proteins and polynucleotides, foreign substances and drugs, which are capable of influencing cell function at the sub-cellular or molecular level are preferably incorporated within the cell in order to produce their effect. For these agents the cell membrane presents a selective barrier which is impermeable to them. The complex composition of the cell membrane comprises phospholipids, glycolipids, and cholesterol, as well as intrinsic and extrinsic proteins, and its functions are influenced by cytoplasmic components which include $Ca^{++}$ and other metal ions, anions, ATP, microfilaments, microtubules, enzymes, and $Ca^{++}$-binding proteins, also by the extracellular glycocalyx (proteoglycans, glycose aminoglycans and glycoproteins). Interactions among structural and cytoplasmic cell components and their response to external signals make up transport processes responsible for the membrane selectivity exhibited within and among cell types.

Successful delivery of agents not naturally taken up by cells into cells has also been investigated. The membrane barrier can be overcome by associating agents in complexes with lipid formulations closely resembling the lipid composition of natural cell membranes. These formulations may fuse with the cell membranes on contact, or what is more common, taken up by pynocytosis, endocytosis and/or phagocytosis. In all these processes, the associated substances are delivered in to the cells.

Lipid complexes can facilitate intracellular transfers also by overcoming charge repulsions between the cell surface, which in most cases is negatively charged. The lipids of the formulations comprise an amphipathic lipid, such as the phospholipids of cell membranes, and form various layers or aggregates such as micelles or hollow lipid vesicles (liposomes), in aqueous systems. The liposomes can be used to entrap the substance to be delivered within the liposomes; in other applications, the drug molecule of interest can be incorporated into the lipid vesicle as an intrinsic membrane component, rather than entrapped into the hollow aqueous interior, or electrostatically attached to aggregate surface. However, most phospholipids used are either zwiterionic (neutral) or negatively charged.

An advance in the area of intracellular delivery was the discovery that a positively charged synthetic cationic lipid, N-[1-(2,3-dioleyloxy)propyl]-N,N,N-trimethylammonium chloride (DOTMA), in the form of liposomes, or small vesicles, could interact spontaneously with DNA to form lipid-DNA complexes which are capable of adsorbing to cell membranes and being taken up by the cells either by fusion or more probably by adsorptive endocytosis, resulting in expression of the transgene [Felgner, P. L. et al. Proc. Natl. Acad. Sci., USA 84:7413-7417 (1987) and U.S. Pat. No. 4,897,355 to Eppstein, D. et al.]. Others have successfully used a DOTMA analogue, 1,2-bis(oleoyloxy)-3-(trimethylammonio)propane (DOTAP) in combination with a phospholipid to form DNA-complexing vesicles. The Lipofectin™ reagent (Bethesda Research Laboratories, Gaithersburg, Md.), an effective agent for the delivery of highly anionic polynucleotides into living tissue culture cells, comprises positively charged liposomes composed of positively charged lipid DOTMA and a neutral lipid dioleyl phosphatidyl ethanol amine (DOPE) referred to as helper lipids. These liposomes interact spontaneously with negatively charged nucleic acids to form complexes, referred to as lipoplexes. When excess of positively charged liposomes over DNA negative charges are used, the net charge on the resulting complexes is also positive. Positively charged complexes prepared in this way spontaneously attach to negatively charged cell surfaces or introduced into the cells either by adsorptive endocytosis or fuse with the plasma membrane, both processes deliver functional polynucleotide into, for example, tissue culture cells. DOTMA and DOTAP are good examples for monocationic lipids. [Illis et al. 2001, ibid.]

Multivalent cations by themselves (including polyalkylamines, inorganic salts and complexes and dehydrating solvents) have also been shown to facilitate delivery of macromolecules into cells. In particular, multivalent cations provoke the collapse of oligo and polyanions (nucleic acids molecules, amino acid molecules and the like) to compact structural forms, and facilitate the packaging of these polyanions into viruses, their incorporation into liposomes, transfer into cells etc. [Thomas T. J. et al. Biochemistry 38:3821-3830 (1999)]. The smallest natural polycations able to compact DNA are the polyalkylamines spermidine and spermine. By attaching a hydrophobic anchor to these molecules via a linker, a new class of transfection vectors, the polycationic lipopolymers, has been developed.

Cationic lipids and cationic polymers interact electrostatically with the anionic groups of DNA (or of any other polyanionic macromolecule) forming DNA-lipid complexes (lipoplexes) or DNA-polycation complexes (polyplexes). The formation of the complex is associated with the release of counterions of the lipids or polymer, which is the thermodynamic driving force for lipoplex and polyplex spontaneous formation. The cationic lipids can be divided into four classes: (i) quaternary ammonium salt lipids (e.g. DOTMA (Lipofectin™) and DOTAP) and phosphonium/arsonium congeners; (ii) lipopolyamines; (iii) cationic lipids bearing both quaternary ammonium and polyamine moieties and (iv) amidinium, guanidinium and heterocyclic salt lipids.

SUMMARY OF THE INVENTION

According to a first of its aspects the present invention provides a sphingoid-polyalkylamine conjugate of the following formula (I):

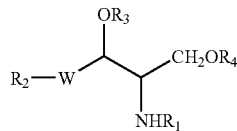

wherein $R_1$ represents a hydrogen, a branched or linear alkyl, aryl, alkylamine, or a group —C(O)$R_5$;

$R_2$ and $R_5$ represent, independently, a branched or linear $C_{10}$-$C_{24}$ alkyl, alkenyl or polyenyl groups;

$R_3$ and $R_4$ are independently a group —C(O)—$NR_6R_7$, $R_6$ and $R_7$ being the same or different for $R_3$ and $R_4$ and represent, independently, a hydrogen, or a saturated or unsaturated branched or linear polyalkylamine, wherein one or more amine units in said polyalkylamine may be a quaternary ammonium; or $R_3$ is a hydrogen; or $R_3$ and $R_4$ form together with the oxygen atoms to which they are bound a heterocyclic ring comprising —C(O)—$NR_9$—[$R_8$—$NR_9$]$_m$—C(O)—, $R_8$ represents a saturated or unsaturated $C_1$-$C_4$ alkyl and $R_9$ represents a hydrogen or a polyalkylamine of the formula —[$R_8$—$NR_9$]$_n$—, wherein said $R_9$ or each alkylamine unit $R_8NR_9$— may be the same or different in said polyalkylamine; and n and m, represent independently an integer from 1 to 10; preferably 3 to 6;

W represents a group selected from —CH═CH—, —CH$_2$—CH(OH)— or —CH$_2$—CH$_2$—;

as well as salts and stereoisomers of said compound of formula (I).

A specific and preferred sphingoid-polyalkylamine conjugate according to the invention is N-palmitoyl D-erythro sphingosyl-1-carbamoyl spermine.

The invention further provides a process for the preparation of a sphingoid-polyalkylamine conjugate of formula (I) as defined herein, the process comprises:

(a) providing a sphingoid compound of formula (I) wherein $R_1$, $R_2$ and W have the meaning as defined above and $R_3$ and $R_4$ represent, independently, a hydrogen atom or an oxo protecting group, wherein at least one of said $R_3$ and $R_4$ represent a hydrogen atom;

(b) reacting said compound of step (a) with an activating agent, optionally in the presence of a catalyst, to obtain an activated $R_3$ and/or $R_4$ group;

(c) reacting said activated sphingoid compound with a polyalkylamine;

(d) removing said protecting group thereby obtaining said sphingoid-polyalkylamine conjugate of formula (I) as defined above.

Yet further, the invention provides a composition comprising a sphingoid-polyalkylamine conjugate of the formula (I) as defined herein, optionally in combination with a physiologically acceptable carrier.

Yet further, the invention provides the use of a sphingoid-polyalkylamine conjugate of formula (I) as defined as a physiologically acceptable delivery vehicle.

Yet further, the invention provides the use of a sphingoid-polyalkylamine conjugate of formula (I) as defined, as a capturing agent.

BRIEF DESCRIPTION OF THE FIGURES

In order to understand the invention and to see how it may be carried out in practice, some embodiments will now be described, by way of non-limiting examples only, with reference to the accompanying figures, in which:

FIGS. 1A-1D show several possible chemical structures, "linear", branched" or "cyclic" lipid like cationic (LLC) compounds which are encompass under the general definition of sphingoid-polyalkylamine conjugate of formula (I), wherein FIG. 1A shows a sphingoid backbone (ceramide) linked to a single polyalkylamine chain, FIGS. 1B and 1C show the same sphingoid backbone linked to two polyalkylamine chains, FIG. 1D shows again the same backbone, however, in which a single polyamine chain is linked via the two hydroxyl moieties to form a cyclic polyamine conjugate.

FIG. 3A presents changes in the concentration of CCS primary amines in a stored dispersion, expressed as percent of primary amines found in freshly prepared (=freshly hydrated) formulation; FIG. 3B presents change in zeta potential during storage; FIG. 3C presents changes in the ratio of the excitation wavelengths 405 nm/380 nm of membrane-incorporated pH-sensitive probe HCPE (1,2-dioleoyl-sn-glycero-3-phosphoethanolamine-N-(7-hydroxycoumarin) [Zuidam N J, Barenholz Y. Biochim Biophys Acta 1329:211-22 (1997); Zuidam N J, Barenholz Y. Biochim Biophys Acta 1368:115-28 (1998)]; FIG. 3D presents change in lipid assemblies' diameter; FIG. 3E presents change in transfection activity.

FIG. 6A presents an image of liposomes comprising CCS chloride salt:Chol (at a ratio of 2:1); FIG. 6B presents an image of liposomes comprising CCS chloride salt:DOPE (at a ratio of 2:1), FIG. 6C presents an image of liposomes comprised of CCS acetate salt:DOPE (at a ratio 2:1), FIG. 7A presents an image of CCS chloride salt based assemblies (worm-like micelles), FIG. 7B presents an image of liposomes in Hepes buffer pH 7.4 comprising CCS chloride:

DOPE (at a ratio 2:1), and FIG. 7C presents an image of liposomes comprising CCS chloride:Chol (at a ratio 2:1).

DETAILED DESCRIPTION OF THE INVENTION

Figures 1A, 1B:
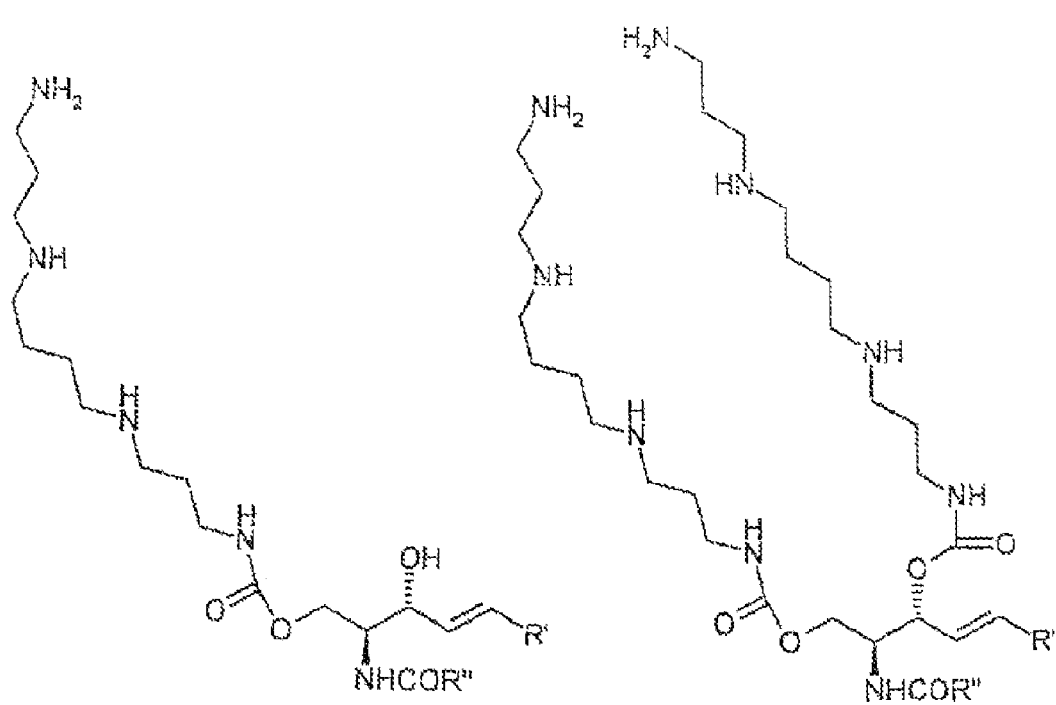

The present invention concerns novel lipid-like cationic (LLC) compounds which may be used, inter alia, as capturing agents and in particular, as vehicles for delivering of polynucleotides, oligonucleotides, proteins, peptides and drugs into cells.

The lipid-like cationic compounds have the following general formula (I), as defined above.

The LLC compound also encompasses salts and stereoisomers of said compound as defined.

The LLC compound of the invention is obtainable, for example, by coupling N-substituted long-chain bases, in particular, N-substituted sphingoids or sphingoid bases together with different polyalkylamines or their derivatives, to form a polyalkylamine-sphingoid entity. The resulting conjugates may be used as is, or further alkylated to obtain one or more quaternary amines within the compound.

Protonation at a suitable pH or alkylation of the formed polyalkylamine-sphingoid entity attributed to the LLC compounds the desired positive charge for interaction with molecules of opposite charge, e.g. biologically active molecules, e.g. for delivery into target cells. The formed LLC compounds, after their synthesis may be directly and efficiently complexed with biologically active molecules in the form of anions, oligoanions or polyanions or macromolecules containing negative charges, to form complexes (lipoplexes).

The term biologically active molecule used herein interchangeably with the term biologically active entity as used herein refers to any biologically active substance having a net negative charge or containing one or more regions or moieties carrying a (local) negative charge, such that under suitable condition it interacts with the net positive charge of the LLC compound of the invention. Non limiting examples of biological entities which may be delivered by the LLC compounds of the invention include: polynucleotides, oligonucleotides, proteins, peptides and drugs.

Interaction or complexation as used herein denotes any type of association known in the art, including electrostatic interaction, or when the LLC compound form micelles and/or vesiculate (e.g. to form liposomes), said association encompass encapsulation of the biological entity within the vesicle, entrapment of the biological entity (in whole or in part) within the lipid-like layer of the vesicle (insertion), electrostatic adsorption to the surface of the micelles or the vesicles or any combination of the above. In the following description, all possible interactions between the LLC compound and the biologically active entity are referred to by the term "complex".

The possible interactions between the LLC compound and the biologically active entity may be referred to by the general term "complexation". The complexes formed between the LLC compound and the biological entity may be suitable as a delivery system, e.g. for targeting such biological entities into cells.

The term capturing agent as used herein refers to the characteristics of the conjugate of the invention to interact with molecules having a negative charge, a negative dipole or a local negative dipole. By said interaction, the conjugate of the invention may be applicable in research which involves, e.g. the identification and isolation, by capturing, of, e.g. biologically active molecules, for example, from an unknown biological sample. The capturing involves electrostatic interaction between the molecule to be captured, carrying a negative charge, a negative dipole or a local negative charge and the positively charged conjugate of the invention. Thus, the conjugate of the invention may also be used in kits, the kits comprising said conjugate of the invention along with instructions how to use the compound as a capturing agent.

The conjugate of the invention may also be used as a delivery vehicle, carrying, by capturing, biologically active molecules as defined above to a target site/into a target cell.

Non-limiting examples of the sphingoids or sphingoid bases which may be used in the contents of the present invention include sphingosine, dihydrosphingosine, phytosphingosine, dehydrophytosphinosine and derivatives thereof. Non-limiting examples of such derivatives include acyl derivatives, such as ceramide (N-acylsphingosine), dihydroceramides, phytoceramides and dihydrophytoceramides as well as ceramines (N-allylsphinogsines) and the corresponding derivatives (e.g. dihydroceramine, phytoceramine, dihydrophytoceramines etc.). The suitably N-substituted sphingoids or sphingoid bases posses free hydroxyl groups which may be activated and subsequently reacted with polyalkylamines to form a polyalkylamine-sphingoid entity. Non-limiting examples of activation agents are N,N'-disuccinimidylcarbonate, di- or tri-phosgene or imidazole derivatives. The reaction of these activation agents with the sphingoids or the sphingoid bases yields a succinimidyloxycarbonyl, chloroformate or imidazole carbamate, respectively, at one or both hydroxyls (depending on the reaction conditions). The reaction of the activated sphingoids with polyalkylamines may yield branched, linear (unbranched) or cyclic polyalkylamine-containing LLC compounds.

Figures 1C, 1D:
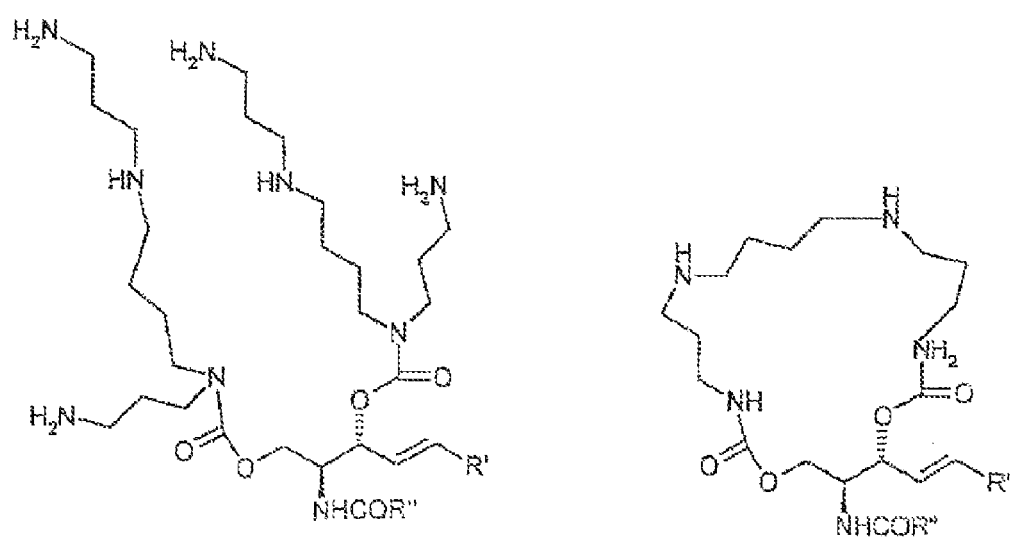

FIG. 1 displays chemical structures of several possible compounds according to the invention. Compound (FIG. 1A) is an example of a LLC compound comprising a single linear polyalkylamine chain; compound (FIG. 1B) consists of two linear polyalkylamine chains; compound (FIG. 1C) consists of two branched polyalkylamine; and compound (FIG. 1D) consists of a cyclic polyalkylamine moiety attached to the sphingoid base via the two oxo groups.

Formation of branched, linear or cyclic polyalkylamine sphingoid conjugates may be directed by monitoring the excess of polyalkylamine used in the reaction and suitable protection of polyalkylamine prior to use.

In the its broadest aspect, the sphingoid-polyalkylamine conjugate of formula (I) as defined herein may be prepared according to the following procedure:

(a) providing a sphingoid compound of formula (I) wherein $R_1$, $R_2$ and W have the meaning as defined above and $R_3$ and $R_4$ represent, independently, a hydrogen atom or an oxo protecting group, wherein at least one of said $R_3$ and $R_4$ represent a hydrogen atom;

(b) reacting said compound of step (a) with an activating agent, optionally in the presence of a catalyst, to obtain an activated $R_3$ and/or $R_4$ group;

(c) reacting said activated sphingoid compound with a polyalkylamine;

(d) removing said protecting group thereby obtaining said sphingoid-polyalkylamine conjugate of formula (I) as defined above.

Protecting groups and their use for protecting active entities within a compound, e.g. an oxo group to which $R_3$ and $R_4$ are bound in the sphingoid compound of the present invention, are well known in the art. Specific, non-limiting examples of such groups include trifluoroacetamide, fmoc, carbobenzoxy (CBZ), dialkyl Phosphoramidates. Other protecting groups may be found in the literature [e.g. in Theodora W. Greene and Peter G. M. Wuts, *Protective Groups in Organic Synthesis,* 2nd Edition, 1980 John Wiley & Sons, Inc. pp 309]

Activating groups for hydroxyl-containing molecules are also known to those versed in the art, and non-limiting examples thereof include N,N'-disuccinimidylcarbonate, di- or tri-phosgene or an imidazole derivative. Other activating agents may be found in the literature [e.g. in Greg T. Hermanson *Bioconjugate Techniques,* Academic Press 1996 pp 142, 183].

Activation of the sphingoid compound, i.e. the oxo to which $R_3$ and $R_4$ are bound, may be achieved in the presence of a catalyst. Non-limiting examples of catalysts include 4-dimethylamino pyridine (DMAP), tetrazole, dicyanoimidazole or diisopropylethylamine.

By the process of the invention it is possible to obtain di-substituted sphingoid-polyalkylamine conjugate carrying identical polyalkylamine substituents. According to one embodiment, the process requires that in step (a) both $R_3$ and $R_4$ are hydrogen atoms, and said process comprises reacting the compound of formula (I) with at least two equivalents of polyalkylamine to obtain a disubstituted sphingoid-polyalkylamine conjugate, with identical polyalkylamine substituents.

By the process of the invention it is also possible to obtain a di-substituted sphigoid-polyalkylamine conjugate carrying different polyalkylamine substituents. According to one embodiment, the process required that in step (a) at least one of $R_3$ or $R_4$ is protected with a protecting group, the process comprises reacting in step (c) the activated sphingoid compound with a first polyalkylamine; removing the protecting group of $R_3$ or $R_4$ to obtain an unprotected oxo group; reacting the unprotected compound with an activating agent to obtain an activated mono-substituted sphingoid-polyalkylamine conjugate; and reacting said activated mono-substituted sphingoid-polyalkylamine conjugate with a second polyalkylamine, thereby obtaining a di-substituted sphingoid-polyalkylamine conjugate, said first and second polyalkylamine may be the same or different.

By the process of the invention it is also possible to obtain a heterocyclic sphingoid-polyalkylamine conjugate. According to one embodiment it is required that in step (a) both $R_3$ and $R_4$ are hydrogen atoms, said sphingoid compound is reacted with at least two equivalents of an activating agent to obtain an activated sphingoid compound wherein both $R_3$ and $R_4$ activated and reacting said activated sphingoid compound with less than an equivalent of polyalkylamine, thereby obtaining a heterocyclic sphingoid-polyalkylamine conjugate.

Evidently modifications of the above described process so as to obtain the different variations of the conjugate of formula (I) also form part of the present invention.

Illustratively, the mono-, di- or heterocyclic sphingoidpolyalkylamine conjugates of the invention are shown in FIGS. 1A-1D.

The formed conjugates of the sphingoids with the polyalkylamines could be further reacted with methylation agents in order to form quaternary amines. The resulting compounds are positively charged to a different degree depending on the ratio between the quaternary, primary and/or secondary amines within the formed conjugates.

A preferred LLC compound according to the invention is a ceramide coupled with spermine, namely, N-palmitoyl D-erythro sphingosyl-1-carbamoyl spermine, which is herein referred to by the abbreviation CCS. In order to determine primary amine concentration in CCS TNBS assay [Barenholz Y. et al. Biochemistry 16:2806-10 (1977)] was performed as described hereinafter.

Figure 2A:
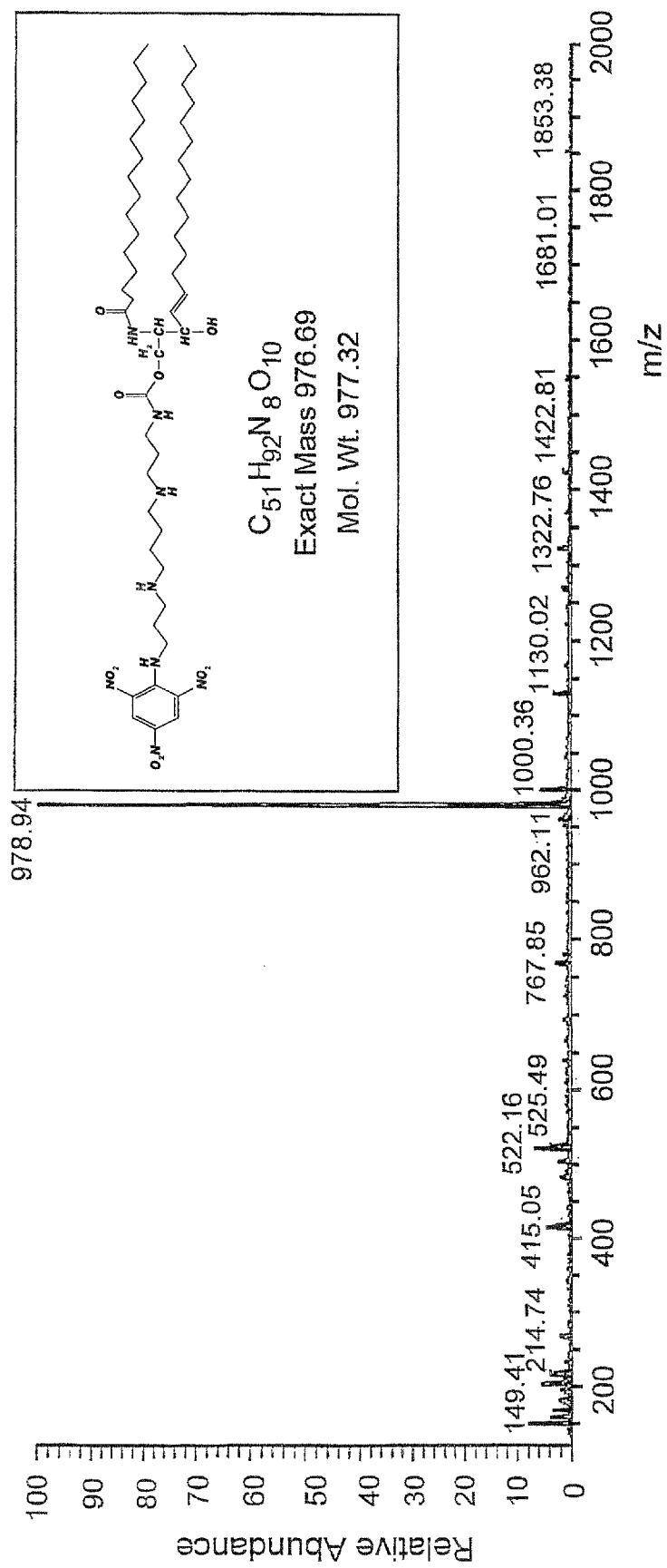
FIGS. 2A-2C show Mass Spectra of a specific LLC compound according to the invention, the N-palmitoyl D-erythro sphingosyl-1-carbamoyl spermine, also referred to as ceramide carbamoyl spermine (CCS) either coupled to 2,4,6-trinitrobenzenesulphonic acid (TNBS) to form TNP-CCS (FIG. 2A) or alone (FIG. 2C), in comparison with spermine coupled to TNBS to form TNP-spermine-TNP (spermine(TNP)$_2$) (FIG. 2B). The chemical structure of each compound is shown as well.
Figure 2B:
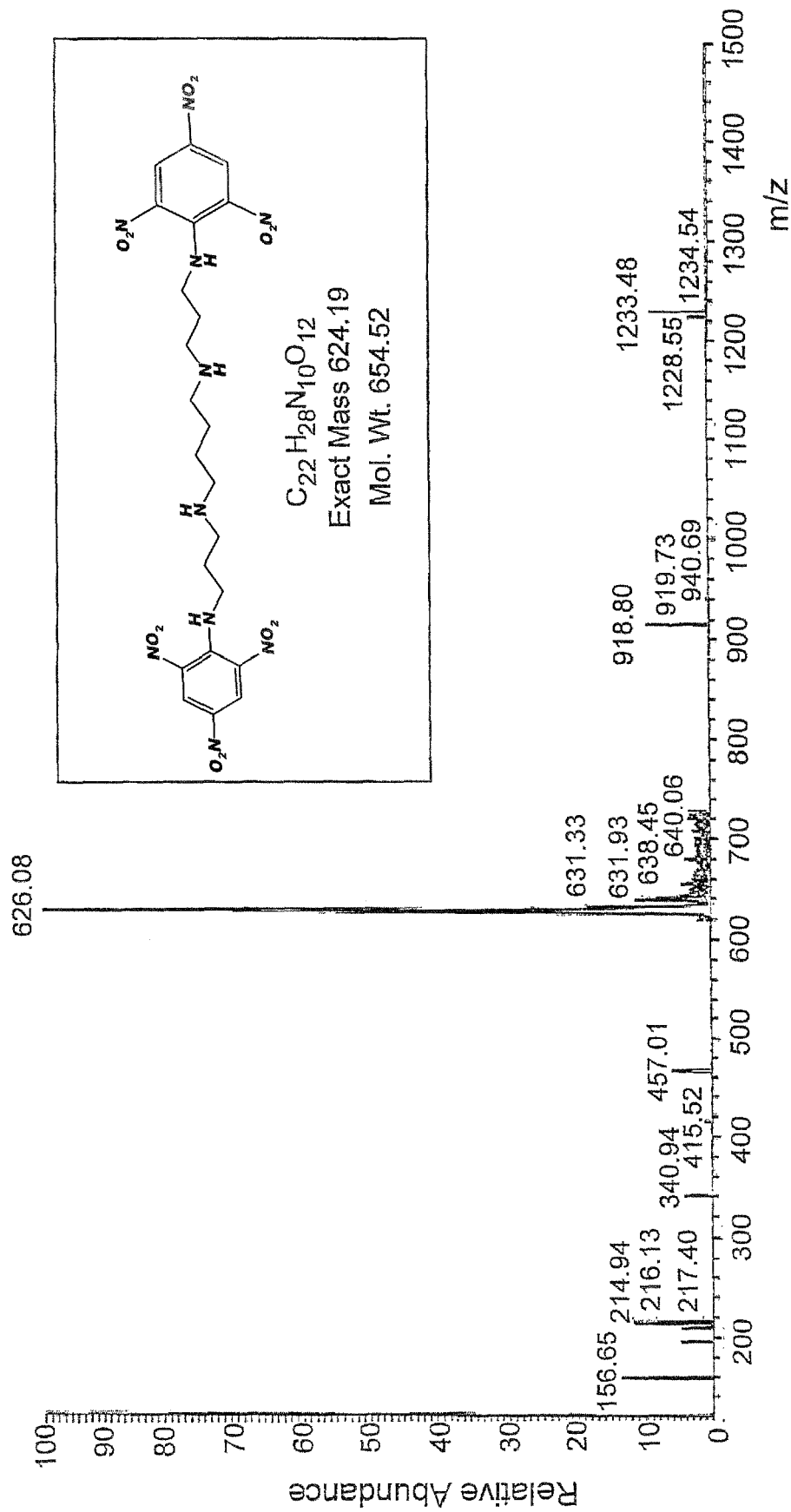

FIGS. 2A-2B present Mass Spectra and deduced chemical structure of products of reacting TNBS with the acetate salt of CCS (FIG. 2A). According to the Mass Spectra of TNBS derivatized CCS to form TNP-CCS, only one primary amine in CCS (peak 978.9) reacted with TNBS. The second amino group of spermine is involved in the carbamoyl linker between spermine and the ceramide primary hydroxyl group at C1 as proved by NMR, i.e. if there were two primary amine groups in the cationic lipid of the invention, they would have both reacted with TNBS. To verify that a second amine did not react with TNBS as a result of steric hindrance, spermine alone was reacted with TNBS. FIG. 2B presents the Mass Spectra of Spermine-(TNP)$_2$, which shows that spermine reacted with TNBS at both free primary amines. The binding of one TNBS per molecule confirmed that CCS contains a single TNBS-reactive primary amine.

Figure 2C:
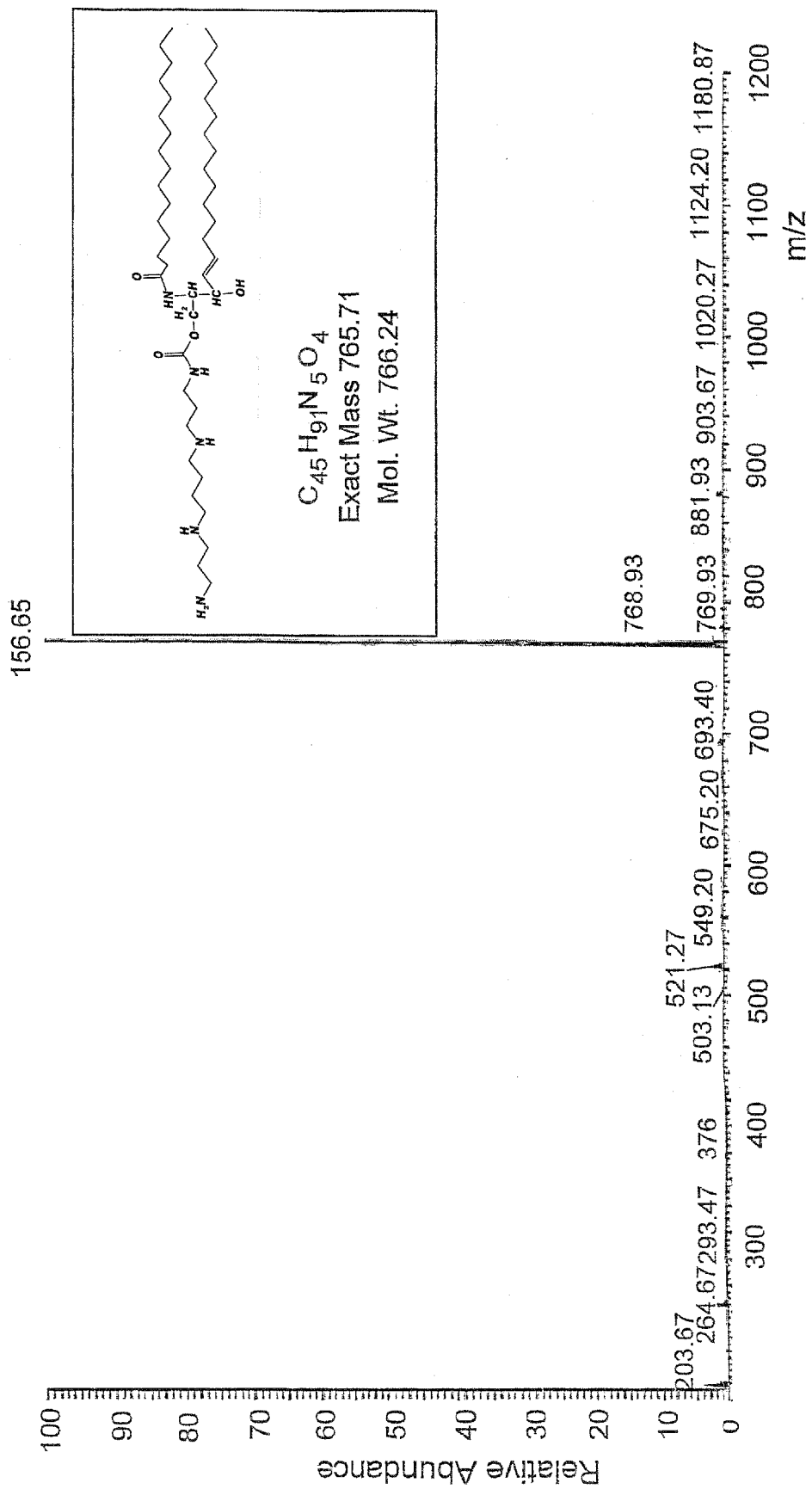

The Expected M.W. of CCS free base (non-protonated) was 766, which was confirmed in the Mass spectra (FIG. 2C). Elementary analysis: C-6.5%; H-11.65%, N-8.01%.

The solubility of CCS in ethanol (base) was also exhibited.

TLC system: Chloroform:Methanol:Acetic acid 1:25:1.5 showed the presence of a single species as a reaction product, i.e. a substantially pure product.

In view of the above it was concluded that the specific CCS compound has only one free primary amine and has the chemical structure shown in FIG. 2C, also representing the Mass Spectra of the compound.

Methylated or non-methylated LLC compounds according to the invention may be processed by any known method to form lipid assemblies including micelles and liposomes. Such processing may include (non-limiting examples) incorporation of different non-cationic lipids like DOPE, Cholesterol or others at different mole ratios to the lipid-like compound. The formed liposomes may be shaped as unsized heterogeneous and heterolamellar vesicles (UHV) having a diameter of about 50-5000 nm. The formed UHV, may be downsized and converted to large (more homoegenous) unilamellar vesicles (LUV) having a diameter of about 50-100 nm by further processing. The structure and dimensions of the vesicles, e.g. their shape and size may have important implications on their efficiency as vehicles for delivery of the active biological entities to the target, i.e. these determine their transfection properties. Thus the structure of the formed vesicles, UHV (unsized heterogeneous) or LUV (large unilamellar), OLV (oligolamellar) and MLV (large multilamellar), is one important factor. Another important factor for efficient delivery is the ratio between the amount of the amine positive charge of the LLC compound ($L^+$) and the negatively charged oligo or polyanion complexed therewith ($A^-$). The ratio determines the overall charge of the charged complex, where for effective delivery the ratio may be $1000<(L^+/A^-)<0.1$, preferably $20<(L^+/A^-)<1$ and more preferably $8<(L^+/A^-)<1.5$ depending on the entrapped/associated moiety.

The following data presents physical characterization of one preferred LLC compound according to the invention, the CCS compound, as an acetate (Acetate/) or chloride salt (Chloride/); in combination with DOPE (ratio of CCS/DOPE 2:1); or in combination with cholesterol (ratio CCS/Chol 2:1).

Critical Micelle Concentration (CMC)

CMC of CCS salts (Acetate and chloride) was measured by changes (increase) in diphenylhexatriene (DPH) fluorescence upon aggregation. The CMC of the acetate salt was equal to that of the chloride salt, both being $5 \times 10^{-6}$ M.

Assembly Size, nm

Size (mass-weight) was measured (by dynamic light scattering) using non-invasive back scattering ALV instrument (ALV GmbH) and the diameter of the different lipid assembly formulations as determined to be:

| | |
|---|---|
| CCS Chloride salt: | micelles 25 nm; |
| CCS Chloride/DOPE 2:1 | liposomes 3594 nm; |
| CCS Acetate salt | micelles 6 nm; |
| CCS Acetate/DOPE 2:1 | liposomes 498 nm; |
| CCS Acetate/Cholesterol 2:1. | liposomes 100 nm-5000 nm; |

Electrostatics of Liposomes and Micelles (with Different Salts and Different Counter-ions)

The pKa of CCS micelles or CCS/DOPE liposomes was determined from the dissociation curve of the pH-sensitive, bilayer-incorporated fluorophore 4-heptadecyl 7-hydroxycoumarin (C17HC) or 1,2-dioleoyl-sn-glycero-3-phosphoethanolamine-N-(7-hydroxycoumarin) (HCPE) ($\Psi_0^{HC}$) [Zuidam & Barenholz (1997) ibid.]. The fluorescence excitation of the fluorophore 7-hydroxycoumarin (HC) moieties at 405 nm for HCPE and 380 nm for C17HC reflects the amount of the ionized species, while the excitation at 370 nm for HCPE and 330 nm for C17HC is the pH-independent isosbestic point, reflects the total amount of probe in the liposomes and micelles. Fluorescence emission was determined at 450 nm for all the above excitations. These two ratios (405/370 for HCPE, and 380/330 for C17HC) give the degree of ionization of HC fluoropore. The titration curve of HC, which is generated by plotting fluorescence excitation intensity ratio $I_{405}/I_{370}$ for HCPE and $I_{380}/I_{330}$ for C17HC at broad range of bulk pH, enables to calculate the apparent pKa of HC in HCPE and C17HC, respectively. The pKa of HC in the liposomal bilayer and/or in the micelles is calculated by fitting the above titration curve to the modified Henderson-Hasselbach equation, as described before [Zuidam & Barenholz (1997) ibid.]. The surface potential is then determined from the shift of pKa of HC that dramatically occurs in the strongly basic environment of cationic bilayer, according to the Boltzmann equation [Zuidam & Barenholz (1997) ibid.]

$$\psi_0^{HC} = \frac{\Delta pK_{el} kT}{e \ln 10}$$

Liposomes' and micelles' ζ-potential was measured at 25° C. by the mobility of the particles in the applied electrical field using a Zetasizer 3000 HAS, Malvern Instruments, Malvern, UK, by diluting an aliquot of 40 μL in 20 mL of 10 mM NaCl (pH 6.7) and passing the solutions before measurement through a 0.2-μm syringe filter (Minisart, Sartorius, Germany). ζ-potential reflects the electrical potential at the plane of sheer (further away from the actual surface), which is sensed by the HCPE and C17HC.

The parameters, which describe lipid assemblies' electrostatics, include surface electrical potential ($\Psi_0^{HC}$); surface pH; and ζ-potential, all of which are presented in the following Table 1:

TABLE 1

Characterization of CCs electrostatics

| Lipid assemblies | pKa | | Surface potential, mV | | Surface pH | | ζ-potential |
|---|---|---|---|---|---|---|---|
| | HCPE | C17HC | HCPE | C17HC | HCPE | C17HC | |
| DOPE/DOPC 1:1 (liposomes) | 10.7 | 8.95 | 0 | ND | 7.4 | ND | 0 |
| CCS Acetate (micelles) | ND | 4.75 | ND | 245.8 | ND | 11.5 | 40 |
| CCS Acetate/DOPE 2:1 (liposomes) | 7.54 | 4.93 | 184.9 | 235.2 | 10.56 | 11.32 | 43.4 |
| CCS Chloride (micelles) | 6.56 | 5.61 | 242.3 | 195.4 | 11.54 | 10.64 | 46.5 |
| CCS Chloride/DOPE 2:1 (liposomes) | 7.41 | 5.94 | 192.5 | 176.15 | 10.69 | 10.31 | 86.8 |
| CCS non-protonated | 7.23 | ND | 203.06 | ND | 10.87 | ND | 34 |
| CCS non-protonated/DOPE 2:1(liposomes) | 8.65 | ND | 119.97 | ND | 9.45 | ND | ND |
| CCS Chloride/Chloride 2:1 (liposomes) | ND | ND | ND | ND | ND | ND | 29.5 |

ND = not determined

Follow Up Assays

The effect of storage in HEPES (pH 7.4) at 4° C. of the cationic lipid, CCS, with or without DOPE (2:1) was also evaluated. FIGS. 3A-3D show the results of the different follow up assays (follow up for 23 days). The follow up assay were based on TNBS test, which is a quantitative assay based on color reaction of TNBS reagent with primary amines.

Figure 3A:
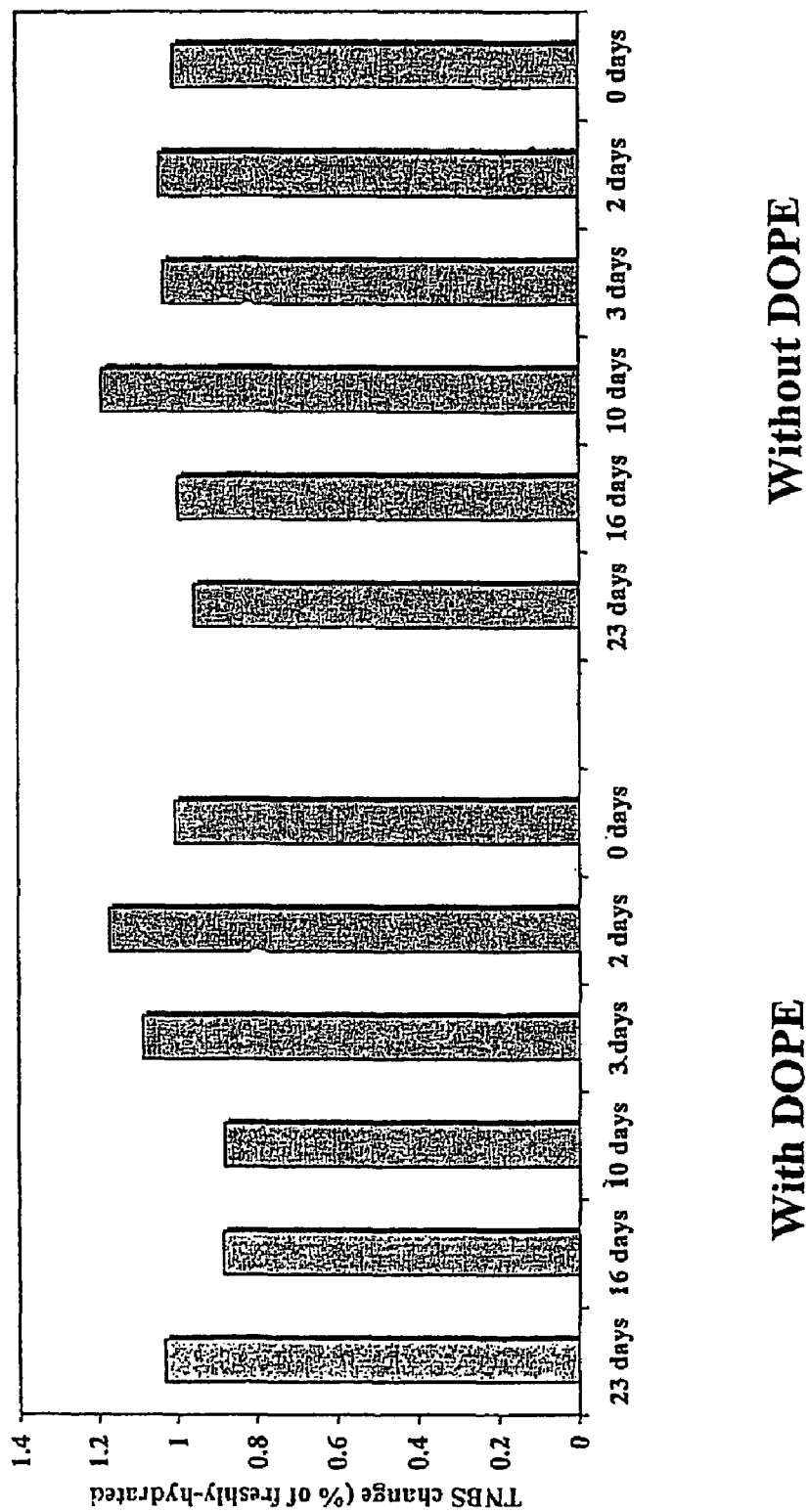
FIGS. 3A-3E show bar graphs of follow up assays upon storage in Hepes buffer pH 7.4 at 4° C. of CCS based lipid assemblies.

In particular, FIG. 3A shows the results of follow up of level of primary amine followed by TNBS binding method (to form TNP derivative) upon storage of CCS-based liposomes, with or without DOPE. It may be concluded from this Figure that both in the presence or absence of DOPE the lipid assemblies formed from LLC compounds, e.g. CCS and a mixture of CCS and DOPE are stable (i.e. there is no substantial change in level of primary amines with time).

Figure 3B:
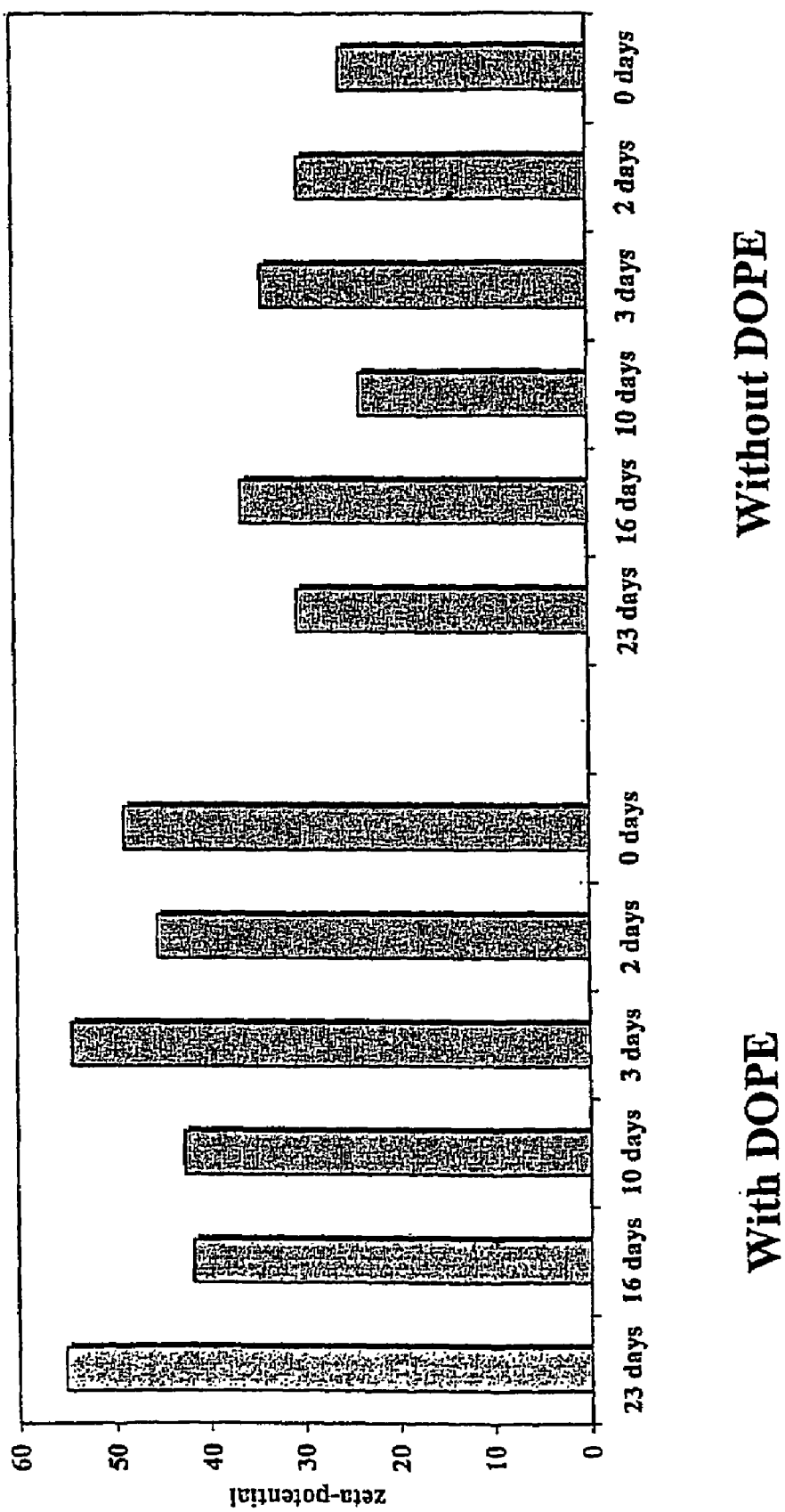

FIG. 3B shows results of the follow up of Zeta potential during storage in HEPES buffer pH 7.4. Also in this case, no substantial change in time was exhibited with respect to the zeta potential. These results are in agreement with the above described integrity of CCS primary amino group (FIG. 3A). Therefore, the minimal changes exhibited in FIGS. 3A and 3B reflect the chemical stability of CCS dispersions in aqueous phase for a period of at least 23 days.

Figure 3C:
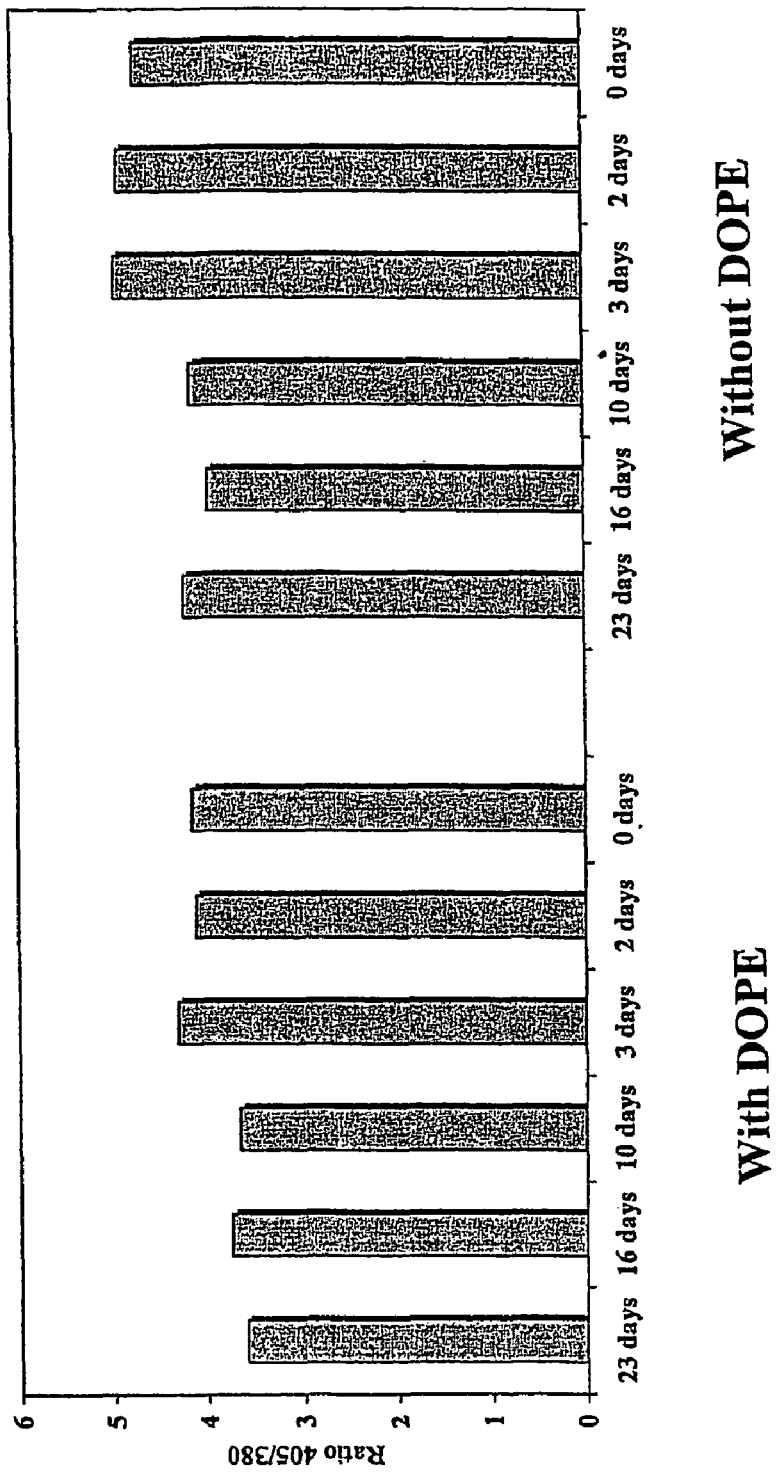

FIG. 3C presents the follow up results of HCPE 405/370 fluorescence excitation intensity ratio which showed that surface pH of cationic liposomes and cationic micelles, and their electrical surface potential $\Psi^0$ (reflected by 405/370 ratio of lipid assembly-incorporated probe HCPE) was unchanged over the entire period of storage, indicating the stability of the surface of CCS.

Figure 3D:
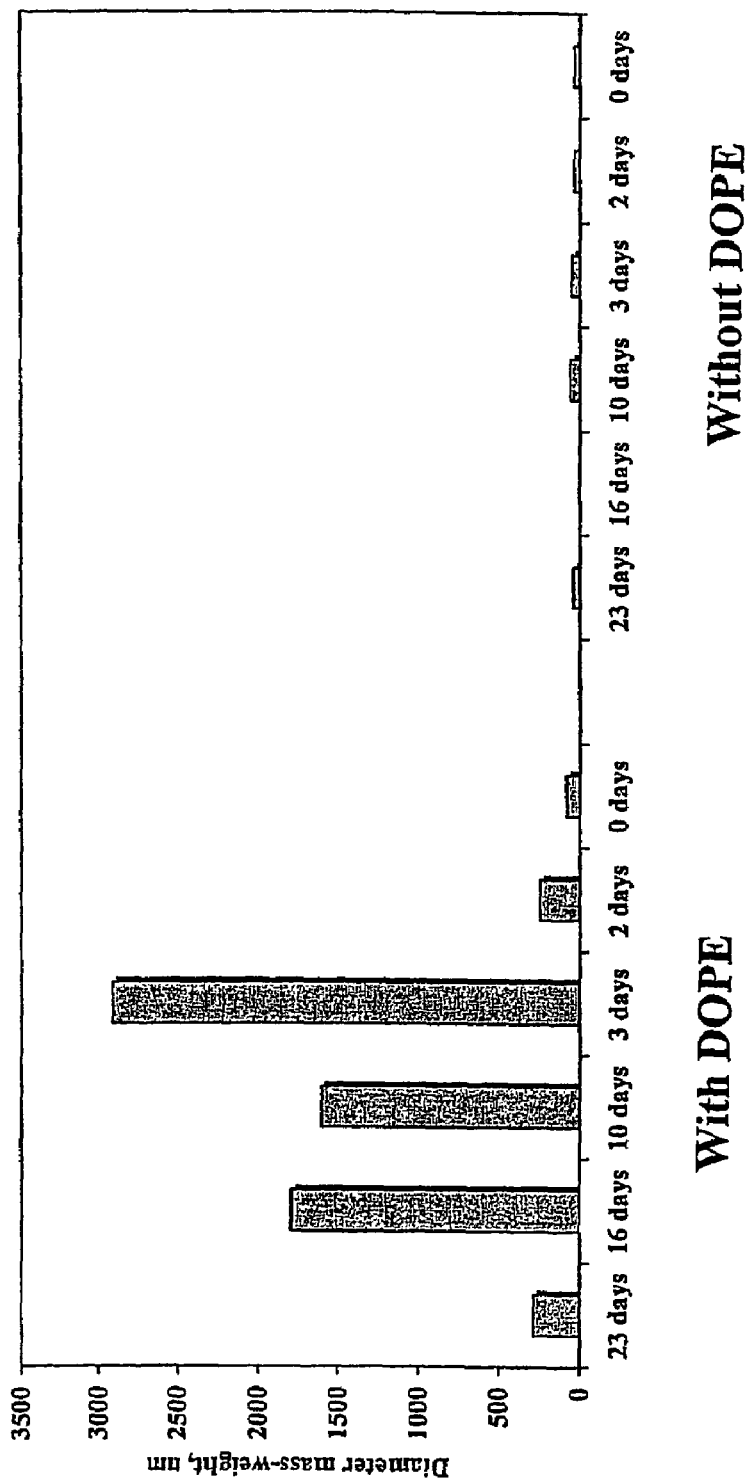

FIG. 3D presents the follow up results of the change in time in the diameter of lipid assemblies. In particular, without DOPE the particles remained relatively small, i.e. in the form of micelles. CCS-DOPE-based assemblies which are UHV are relatively much larger than micelles and they tend to aggregate during storage, leading to size increase. However, the aggregations to their original size distribution occurred upon short (10 sec) ultrasonic irradiation as described below.

Figure 3E:
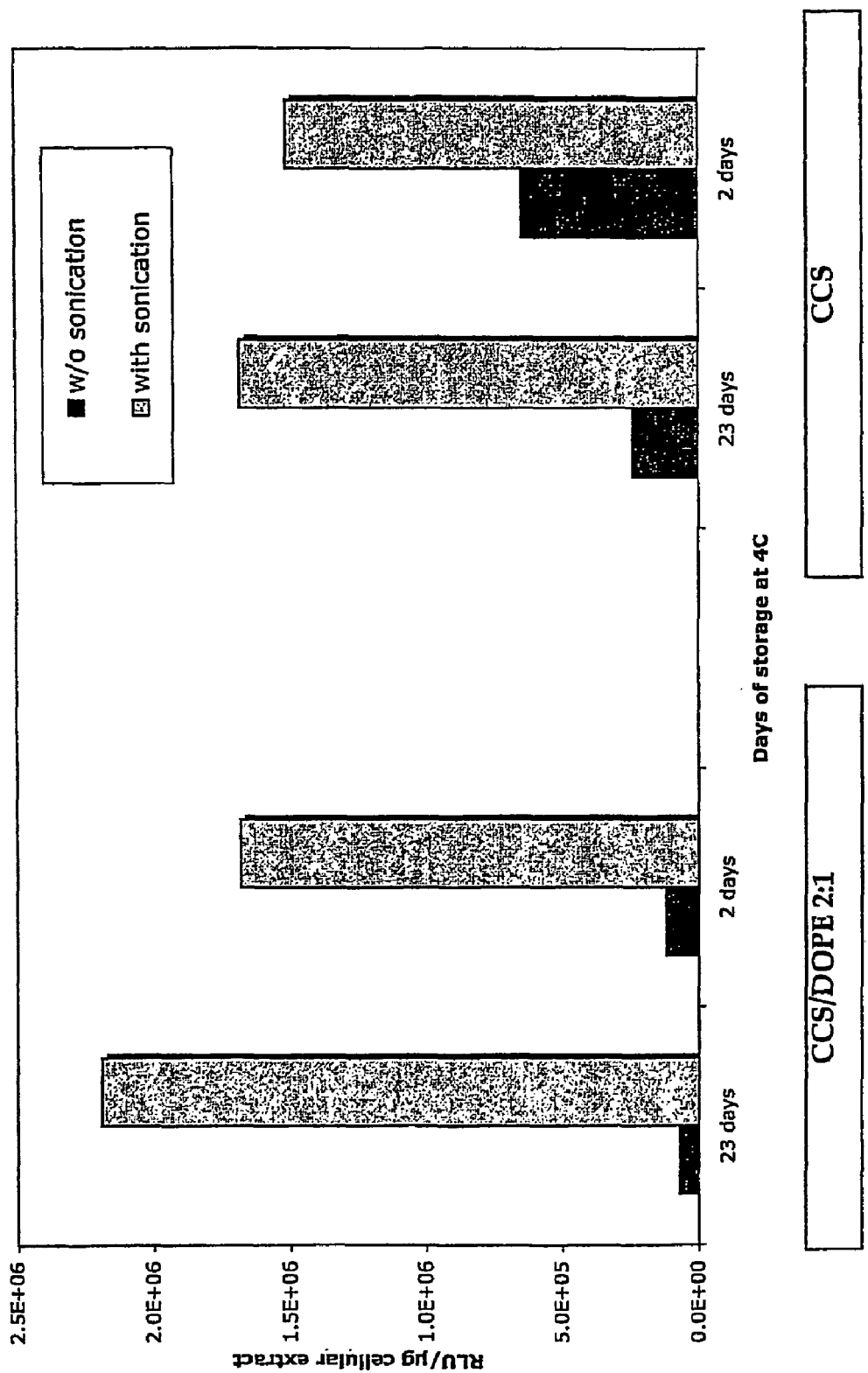

FIG. 3E presents results of follow up of the transfection activity. Generally, the transfection activity was assessed by luciferase expression (see methods of transfection). In view of aggregation upon storage (FIG. 3D), the lipid dispersions before preparation of lipoplexes were sonicated on Elma TRANSSONIC 460/H bath sonicator for 10 s. Only 2- and 23-day points are shown. The conclusions which may be drawn from the results of the follow-up assays are as follows:
- No substantial degradation of lipid or modification of amines occurred upon storage in aqueous dispersion form in HEPES buffer (pH 7.4) at 4° C. (based on content of primary amines) up to 23 days and on surface and zeta-potential;
- Decrease in transfection activity due to aggregation occurred; however, this was easily overcome by sonication of the lipid assemblies by 10 seconds sonication, which resulted in the dissociation of the aggregates to the original size distribution and in complete recovery of transfection efficiency to the level of fresh preparation.

Figure 4:
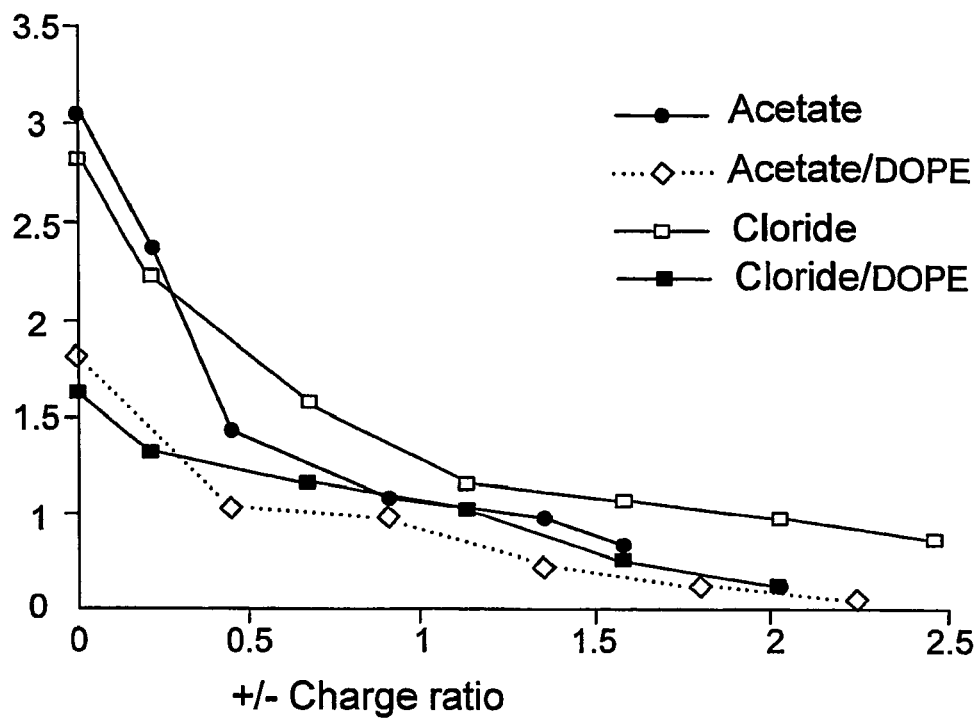
FIG. 4 shows the effect of titration of different lipid assemblies (liposomes and micelles) comprising CCS with plasmid DNA on the electrical surface potential as determined by the pH and electrical potential probe, 4-heptadecyl-7-hydroxycoumarin (C17HC).

Effect of Complexation of CCS Containing Assemblies with DNA on Electrostatics and Hydration The results of titration of the different CCS-based liposomes with plasmid DNA is presented in FIG. 4. Titration was monitored by changes in bilayer-incorporated C17 HC 380/330 fluorescence excitation ratio (emission read at 450 nm) upon addition of DNA. In FIG. 4 the acetate salt of CCS is termed "Acetate", the CCS acetate salt/DOPE (mole ratio 2:1) formulation is termed "Acetate/DOPE", the CCS chloride salt is termed "Chloride" and the combined chloride salt and DOPE (ratio 2:1) is termed "Chloride/DOPE".

Level of Hydration

Hydration level of the different CCS-based lipid assemblies before and after the addition of plasmid DNA was determined by monitoring changes of "Laurdan excitation general polarization" according to which the higher the value obtained, the lower is the level of hydration.

Laurdan GP Fluorescence Measurements

6-Dodecanoyl-2-dimethylaminonaphthalene (Laurdan), purchased from Lambda (Graz, Austria), was used to follow changes in hydration level of the liposome bilayer. The naphthalene fluorophore of this probe is located at the hydrophilichydrophobic interface of the bilayer, and its 12-carbon chain is aligned parallel to the bilayer lipid acyl chains. When associated with lipids, Laurdan excitation and emission spectra depend strongly on the phase of the lipid. The differences in spectra at different phases are due to the SO phase being less hydrated than the LD phase in the lipid headgroup region. The lipid phases and level of hydration can be described by a Laurdan steady-state fluorescence parameter referred to as generalized polarization (GP) [Hirsch-Lerner D, Barenholz Y. Biochim Biophys Acta. 1461(1):47-57 (1999)]. Laurdan GP fluorescence spectra in lipid vesicles are dependent on the number of water molecules around the fluorescent moiety of Laurdan. Excitation GP was calculated according to the expression:

$$GP_{340}=(I_{440}-I_{490})/(I_{440}+I_{490}) \qquad (1)$$

where $I_{440}$ and $I_{490}$ are the intensities of fluorescence emission at wavelengths 440 and 490 nm and the excitation wavelength 340 nm.

Figure 5:
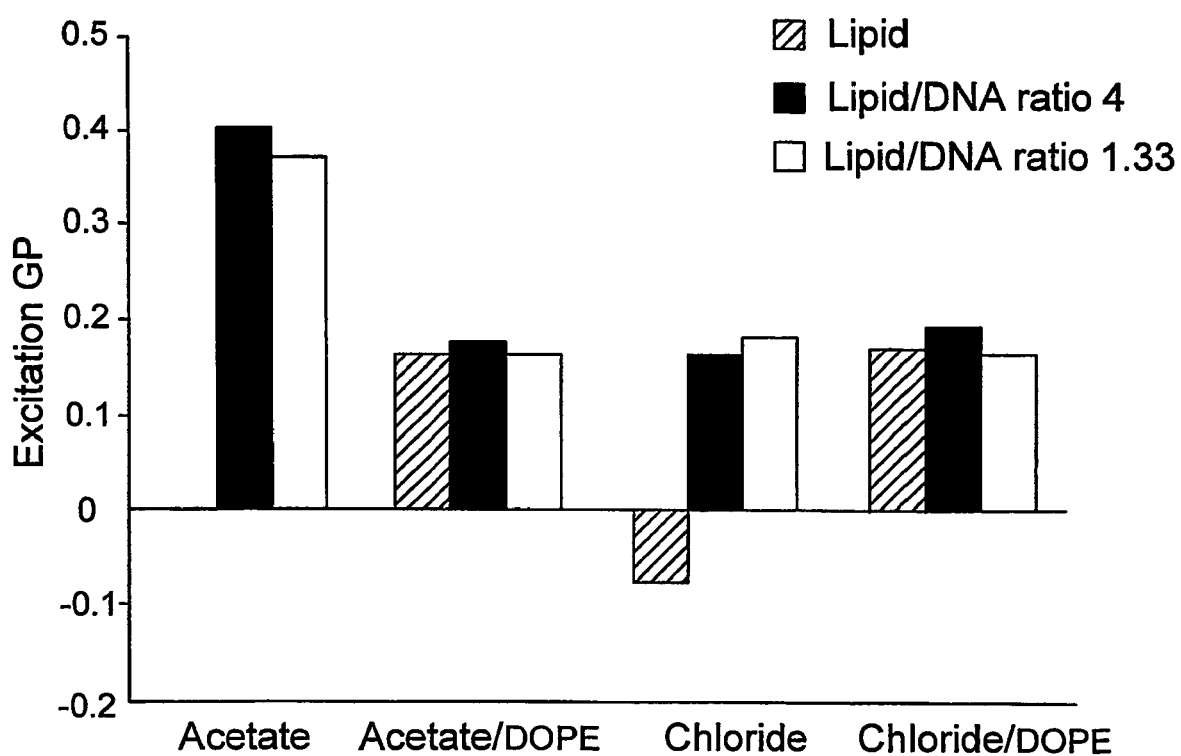
FIG. 5 shows level hydration of different CCS based assemblies (acetate salt, acetate salt/DOPE combination, Chloride salt, or chloride salt/DOPE combination) before ("lipid") and after addition of plasmid ("lipid/DNA" at two different ratios), as determined semi-quantitatively through general excitation fluorescence polarization of the fluorescent probe Laurdan [Hirsch-Lerner D. and Barenholz Y. Biochim Biophys Acta. 1461(1):47-57 (1999)].

An aliquot of Laurdan-labeled liposomes was diluted with 1 mL of 20 mM HEPES buffer (pH 7.4) to the desired concentration, followed by addition of different amounts of DNA. Fluorescence measurements were carried out at temperature 25° C. on a Perkin Elmer LS50B luminescence spectrometer using a 1-cm light path. The results obtained are presented in FIG. 5, which shows that liposomes CCS/DOPE or micelles CCS are in a high hydration state, but become dehydrated upon addition of DNA (formation of lipoplexes), which is signified by sharp increase in Laurdan GP value.

Morphology and Structure of CCS-based Lipid Assemblies and Lipoplexes

Figure 6A:
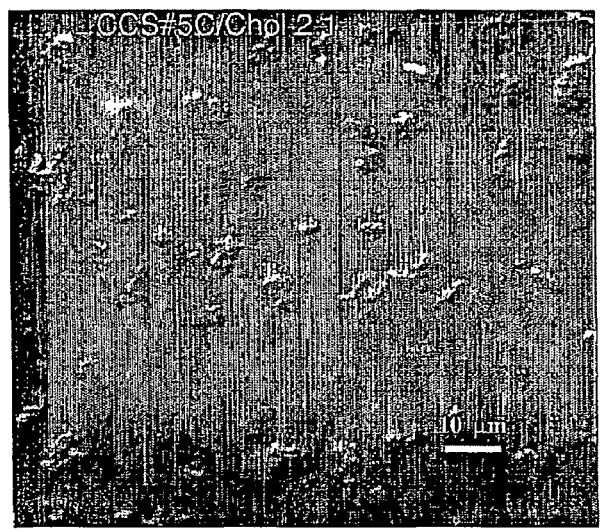
FIGS. 6A-6C show light microscopy images and in particular.
Figure 6B:
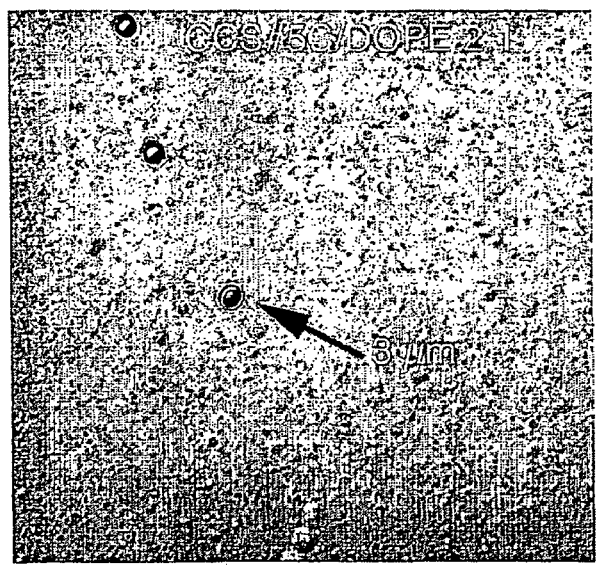
Figure 6C:
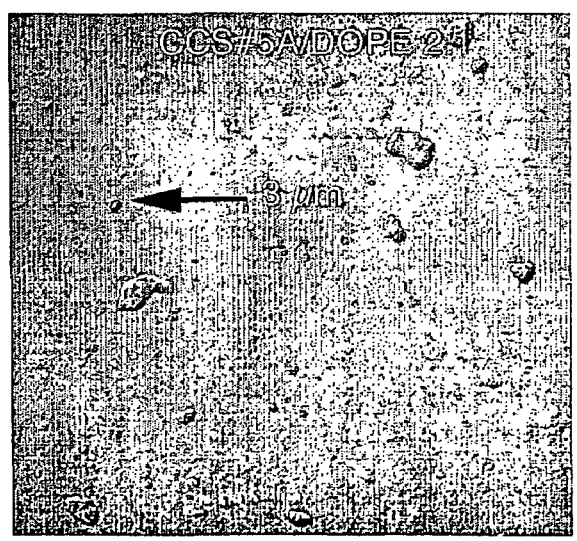
Figure 7A:
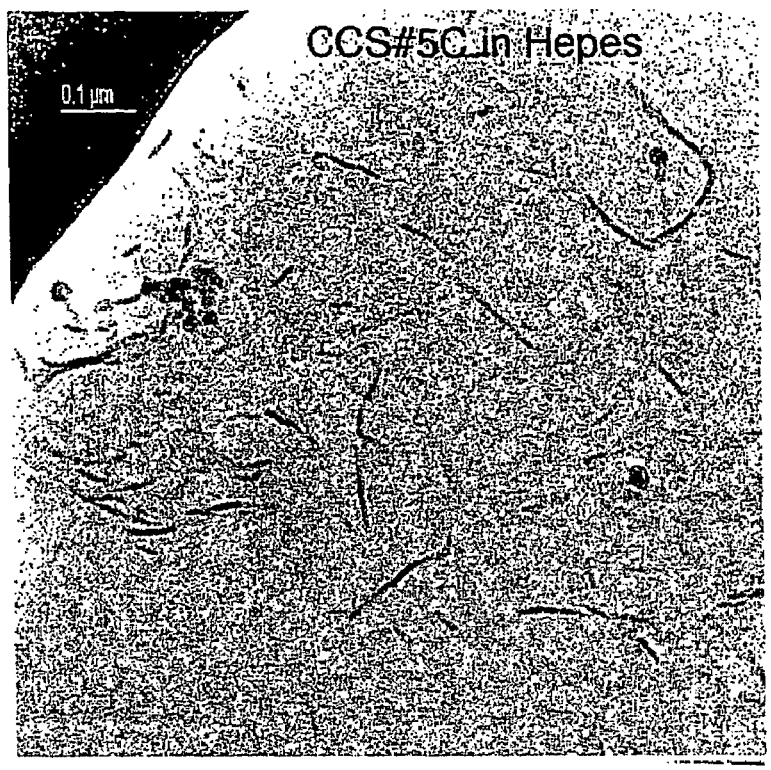
FIGS. 7A-7C present Cryo-TEM images and in particular.
Figure 7B:
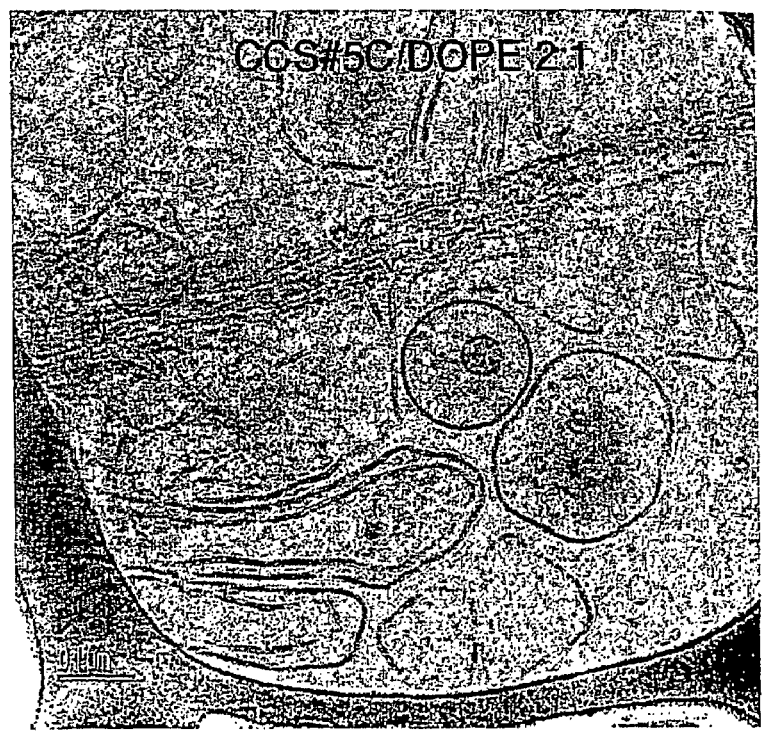
Figure 7C:
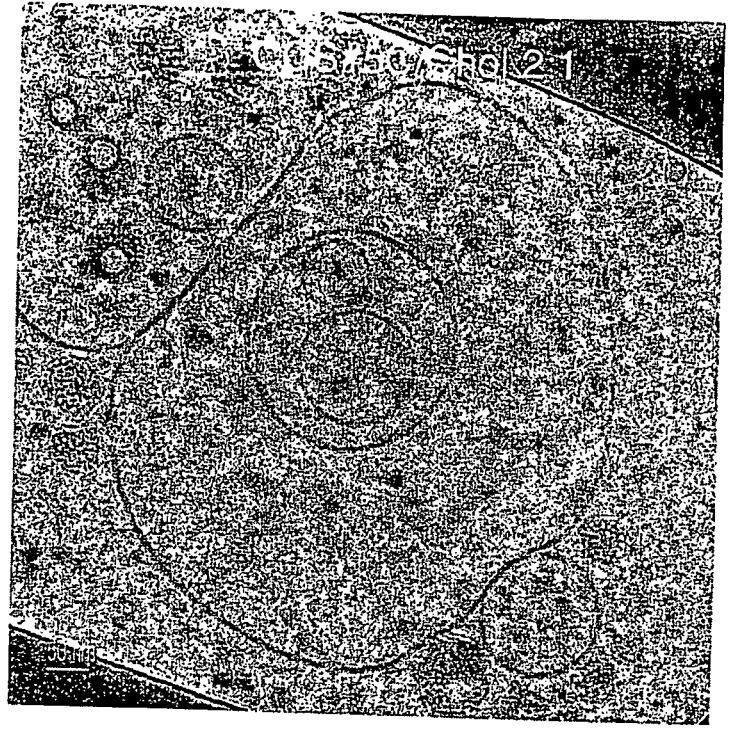

Finally, light microscopy (FIGS. 6A-6C) and Cryo-TEM images (FIGS. 7A-7C) were obtained and the respective images are presented: FIG. 6A presents a light microscope image of liposomes comprised of CCS chloride salt:Chol (at a ratio of 2:1); FIG. 6B presents a light microscope image of liposomes comprised of CCS chloride salt:DOPE (at a ratio of 2:1), FIG. 6C presents a light microscope image of liposomes comprised of CCS acetate salt:DOPE (at a ratio 2:1), FIG. 7A presents a Cryo-TEM image of CCS chloride salt based micelles in Hepes, FIG. 7B presents a Cryo-TEM image of liposomes in Hepes comprised of CCS chloride: DOPE (at a ratio 2:1), FIG. 7C presents a Cryo-TEM image of micelles in Hepes comprised of CCS chloride:Chol (at a ratio 2:1).

Efficiency of CCS-based lipid assemblies in delivery of nucleic acids and proteins determined through biological activity. Biological efficiency of CCS-based nucleic acid and amino acid lipoplexes.

Transfection with the LLC compound of the invention may facilitate, for example, vaccination, introduction of genes into cells for their expression, gene and oligo- and poly-nucleotide therapy. In addition, liposomes and micelles formed by the LLC compound of the invention were found to efficiently induce on mice peritoneal macrophage surface the expression of high levels of MHC II and co-stimulatory molecules such as B7 and CD40 (data not shown). These are essential for productive antigen presentation. Neutral and anionic liposomes seem not to possess such abilities.

Thus, the formed complexes according to the invention may be part of a pharmaceutical composition comprising the complex carrying an active biological entity to be delivered together with suitable excipients, preferably, physiologically acceptable carriers. Such pharmaceutical compositions may be prepared for, e.g. intravenous, subcutaneous, topical, intranasal, oral, ocular or intramuscular in vivo administration as well as ex vivo and in vitro (cell culture) applications.

The physiologically acceptable carrier according to the invention generally refers to inert, non-toxic solid or liquid substances preferably not reacting with the biologically active molecule or with the conjugate and which is required for the effective delivery of the conjugate with the biologically active molecule. The assemblies forming part of the composition of the invention are typically in the form of suspensions or dispersions.

Non-limiting examples of physiologically acceptable carrier include water, saline, 5% dextrose (glucose), 10% sucrose etc., either alone or with minor amounts (up to 10%) of an alcohol, such as ethanol.

One more specific example of efficient use of the LLC compounds vehicles is in oligonucleotide transfer into cells, and in particular into cancerous cells. One approach in cancer treatment is to target specified poly- or oligo-nucleotides in the form of antisense in order to interfere with cancer cell function.

Another use of the LLC vehicles of the invention is in vaccination. Accordingly, antigens may be complexed (either encapsulated within the vehicle, entrapped in the lipid-like layer, associated at the surface of the vehicle etc. or mere complexation) with the LLC compound to form an antigenic entity (a vaccine). The complex may further include immunostimulants or any other biologically active compounds facilitating the desired modulation (stimulation, enhancement etc.) of the immune response.

In particular, CCS-Antigen (biologically active molecules) formulations were found to have superior pharmacokinetics over antigens alone; antigens associated with negatively charges liposomes or even than DOTAP (monocationic lipid) based vaccines. CCS based vaccine was the only vaccine that was capable of delivering the antigen to the nasal lymph nodes (data not shown).

EXAMPLES

Chemistry

Example 1

Synthesis of N-palmitoyl D-erythro sphingosyl-1-carbamoyl spermine (CCS)

(i) N-palmitoylsphingosine (1.61 g, 3 mmol) was dissolved in dry THF (100 ml) with heating. The clear solution was brought to room temperature and N,N'-disuccinimidyl carbonate (1.92 g, 7.5 mmol) was added. DMAP (0.81 g, 7.5 mmol) was added with stirring and the reaction further stirred for 16 hours. The solvent was removed under reduced pressure and the residue re-crystallized from n-heptane yielding 1.3 g (68%) of disuccinimidylceramidyl carbonate as white powder m.p. 73-76° C.

(ii) Spermine (0.5 g, 2.5 mmol) and the disuccinimidylceramidyl carbonate (0.39 g, 0.5 mmol) were dissolved in dry dichloromethane with stirring and then treated with catalytic amount of 4-dimethylamino pyridine (DMAP). The solution was stirred at room temperature for 16 hours, the solvent evaporated and the residue treated with water, filtered and dried in vacuo, giving 0.4 g (82%) of crude material which was further purified by column chromatography on Silica gel, using 60:20:20 Butanol:AcOH:$H_2O$ eluent.

(iii) For obtaining a quaternary amine within the compound, the product of step (ii) may be methylated with DMS or $CH_3I$.

Example 2

Other Synthetic Procedures

Similarly to the above procedure, the following procedures may be applied:

Synthesis of Linear Monosubstituted Ceramde-spermine Conjugate as Depicted in FIG. 1A An equivalent of a ceramide is reacted with 2.5 equivalents of disuccinimidyl carbonate in the presence of DMAP to obtain the corresponding 1,3-di-O-succinimidyl derivative is obtained.

The disuccinimidyl derivative though obtained is reacted with an equivalent of spermine at room temperature using catalytic amount of DMAP to obtain the 3-monosubstituted ceramide-spermine conjugate of FIG. 1B.

Synthesis of Linear Disusbstituted Ceramide-spermine Conjugate as Depicted in FIG. 1B An equivalent of 1,3-di-O— succinimidyl sphinogid derivative prepared as described above is reacted with 2.5 equivalents of spermine at 80° in the presence of catalytic amounts of DMAP. The 1,3-disubstituted CCS is though obtained.

Synthesis of Linear Disusbstituted Ceramide-branched Spermine Conjugate as Depicted in FIG. 1C An equivalent of 1,3-di-O-succinimidyl ceramide derivative prepared as described above is reacted with 2.5 equivalents of alpha-omega di protected spermine at 80° in the presence of catalytic amounts of DMAP.

The protection is removed and the 1,3-"branched" disubstituted ceramide-spermine conjugate is obtained.

Synthesis of Linear Disusbstituted Ceramide-cyclic Spermine Conjugate as Depicted in FIG. 1D An equivalent of 1,3-di-O-succinimidyl ceramide derivative prepared as described above is reacted with 0.75 equivalents of spermine at 80° C. in the presence of catalytic amounts of DMAP.

Example 3

Chemical characterization of N-palmitoyl D-erythro sphingosyl-1-carbamoyl spermine TNBS assay was used to determine primary amines per CCS molecule in the exemplified cationic lipid of the invention. Accordingly, the tested compound, CCS, (100 ml) was added to bicarbonate solution (500 µl, pH 8.4) followed by the addition of TNBS (1200 nmol, 20 µl). The mixture was incubated for 30 min. After incubation, acetic acid was added (20 µl). Red sediments were spun down and dissolved in acetonitrile. Mass spectra of the specific compound TNP-CCS were obtained. For structure analysis TNBS assay was also performed on spermine.

The following parameters were determined for the exemplified lipid assemblies:
  Critical micelle concentration (CMC) was determined by measuring the change in diphenyl hexatriene (DPH) fluorescence upon aggregation;
  Liposome size was determined by dynamic light scattering using non-invasive back scattering ALV instrument (ALV GmbH).
  Surface potential and surface pH of the CCS-based assemblies were determined from the dissociation curve of hydroxycoumarin (HC) moiety of C17HC or hydroxycoumarin phosphatidyl ethanolamine (HCPE) incorporated in the assemblies.
  Zeta potential was determined in 10 mM NaCl with Zetasizer (Malvern instruments).

Titration of CCS-based Lipid Assemblies with Plasmid DNA
  A small aliquot of liposomes and micelles (typically 20-40 mmol) with incorporated C17HC was added to the 1 cm quartz cuvette containing HEPES 20 mM pH 7.4 and ratio of excitation wavelengths 380/330 was recorded using emission at 450 nm. Then, various amounts of DNA were added to produce charge ratios stated in FIG. 4. While recording the ratio 380/330. In this connection, the following additional parameters were determined:

Change in level of hydration of CCS-based lipid assemblies upon complexation with DNA Hydration before and after addition of plasmid DNA was monitored by determining the changes of Laurdan excitation General Polarization as described by Hirsch-Lerner and Barenholz [Hirsch-Lerner and Barenholz (1999) ibid.]. According to this procedure, the higher value obtained indicates a lower level of hydration.

Stability of CCS-based Lipid Assemblies in Aqueous Dispersion

The effect of storage in HEPES buffer (pH 7.4) at 4° C. on CCS either alone (micelles), or in combination with DOPE (mole ratio 2:1 UHV liposomes) was determined. The level of primary amines was determined with storage time in TNBS binding and described as % of freshly hydrated preparation. The change in Zeta potential, the change in the HCPE fluorescence 450 nm/370 mnm excitation ratio, and the change in size of the lipid assemblies (liposomes or micelles) formed was determined.

Storage Assays

The corresponding lipid assemblies (CCS or CCS/DOPE 2:1) were prepared as described above, by reconstitution in Hepes buffer, stored from 0 to 21 days at 4 C. At 21 day, there were 6 time points of storage, which were assayed simultaneously for the following parameters:

Surface potential (HCPE)

Zeta-potential

Size

Primary amine (TNBS)

Transfection Efficiency

The results are presented in FIGS. 3A-3E. The conclusion is that among all the parameters tested, the only physical change was aggregation of liposomes with time, which led to reversible reduction of transfection activity but this effect could be overcome by a brief (10 sec) sonication of the liposomes. Electrostatic parameters (zeta potential and surface potential) and number of primary amines remained unchanged.

Materials

Monocationic lipid DOTAP (N-(1-(2,3-dioleoyloxy)propyl), N,N,N-trimethylammonium chloride); neutral lipid DOPE (1,2-dioleoyl-sn-glycero-3-phosphatidyl ethanolamine) were all from Avanti Polar Lipids (Alabaster, Ala.).

4-heptadecyl-7-hydroxycoumarin was obtained from Molecular Probes (Oregon USA)

Cholesterol was from Sigma.

The pH-sensitive probe 7-hydroxycoumarin-phosphatidylethanolamine (HCPE) was prepared by labeling of DOPE primary amine with 7-HC succinimidyl ester (Molecular Probes), according to the amine labeling procedure of Molecular Probes (Eugene, Oreg.).

Trinitro benzene sulfonic acid (TNBS) and Hepes were from Sigma.

6-dodecanoyl-2-dimethylaminonaphthalene (laurdan) and, 6-diphenyl-1,3,5-hexatriene (DPH) were obtained from Molecular probes

DNA

The following plasmids were used:

(1) Commercially available plasmid pQBI 25 coding for green fluorescent protein (GFP) variant under control of CMV promoter-enhancer (Qbiogene, Montreal, Canada);

(2) pCMV-EYFP$_{mito}$, a plasmid coding for enhanced yellow fluorescent protein (EYFP), carrying mitochondrial localization signal, was purchased from BD Biosciences Clontech, Palo Alto, Calif. pCMV-Luc coding for the luciferase gene was constructed by insertion of a 875-bp CMV promoter-enhancer fragment into pGL3-enhancer (Promega, Madison, Wis.);

All plasmids were propagated in E. coli and purified in sterile endotoxin-free form using the QIAGEN EndoFree Plasmid Mega kit (QIAGEN, Hilden, Germany) according to the manufacturer's protocol, and were analyzed for purity and topology as described (Even-Chen and Barenholz, 2000).

Microscopy

For study of liposome size distribution, a drop of the lipid dispersion was placed on a slide, covered with a cover glass, and viewed in transmitted mode using Nomarsky contrast. The slides were viewed on an Olympus FV300 laser scanning microscope (Olympus Optical, Japan). For estimating size of aggregates, 3-µm latex beads (Sigma) were added to the formulations.

The Cryo-transmission Electron Microscopy

For each experiment, lipid dispersions at concentrations of 10 mM cationic lipid were prepared in 20 mM HEPES buffer, pH 7.4. The vitrified specimens were prepared in a controlled environment vitrification system (CEVS) at 25° C. and 100% relative humidity. Samples were examined in a Philips CM120 microscope operated at 120 kV. Specimens were equilibrated in the microscope below −178° C., then examined in the low-dose imaging mode to minimize electron beam radiation damage, and recorded at a nominal underfocus of 4-7 nm to enhance phase contrast. An Oxford CT-3500 cooling holder was used. Images were recorded digitally by a Gatan MultiScan 791 CCD camera using the Digital Micrograph 3.1 software package.

CMC Determination with DPH

DPH dissolved in fetrahydrofuran was added at concentration of 0.25 ml %, to a range of concentrations of lipid dispersions and the fluorescence was recorded using 360 nm excitation and 430 nm emission on Perkin Elmer LS-50B. Then the fluorescence was plotted as function of lipid concentrations, and CMC point was detected as change of the slope of the curve by intersection of two straight lines above or below the CMC region.

Structural Analysis of Spermine-Ceramide Conjugate Using NMR Spectroscopy

One-dimensional NMR Studies

NMR experiments were performed and spectra were collected on Varian Inova in the resonance frequency of 500 MHz spectrometer equipped with a 5 mm computer switchable probe. Chemical shift were processed using the standard VNMR software using 500 MHz for $^1$H and $^{13}$C frequencies, respectively. Ceramide sample was dissolved in CDCl$_3$ while ceramide-spermine conjugate was used as triacetate salt and dissolved in deuterated methanol (CD4O). For conformational analysis of the ceramide-spermine conjugate, temperature range between 0° C. to 40° C. was investigated. In all case the peak of hydrated solvent was use as internal reference.

Two-dimensional NMR Experiments

Figure 8:
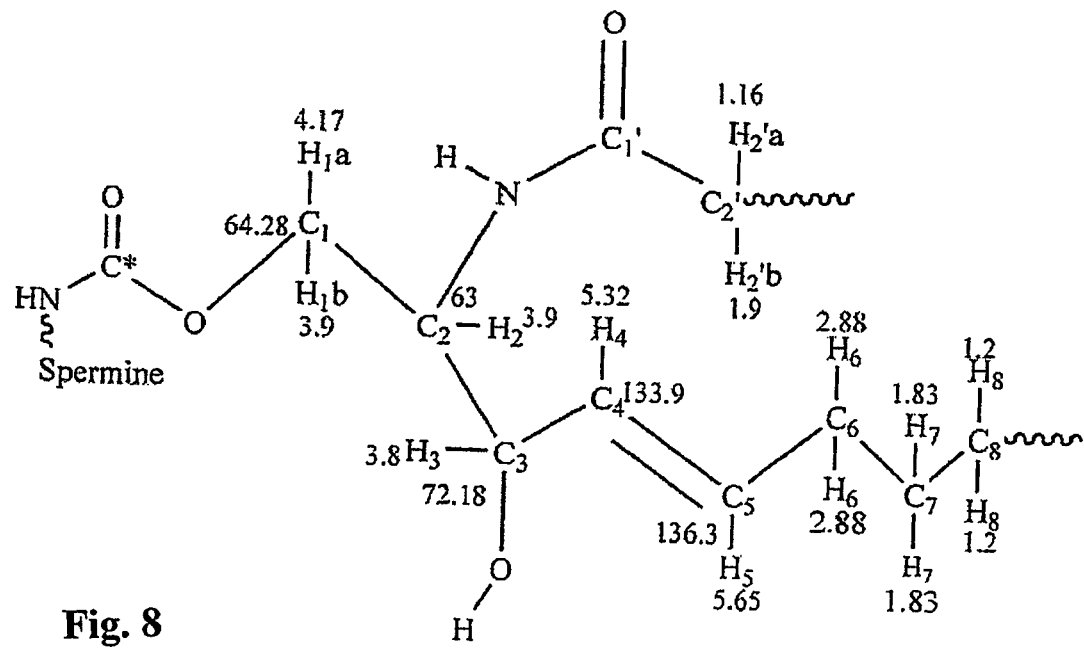
FIG. 8 presents the structure and numbering of the central region of CCS, including assignment of the $^1$H and $^{13}$C of CCS as obtained from two dimensional NMR experiments described herein.

The $^1$H-$^1$H correlation spectroscopy (COSY) and $^1$H-$^{13}$C heteronuclear multiple quantum coherence (HMQC) experiments were carried out with an inverse probe. Due to solubility obstacles, the triacetate salt in deuterated methanol (CD4O) was used. The assignment shown in Tables 3 and 4 (see FIG. 8 for numbering) is outcome of data collected from one dimensional $^1$H- and $^{13}$C-NMR together with two dimensional experiments. There are two possible/conjugation sites at spermine one is the hydroxyl group HO(C1) and the other is HO(C3). The conjugation of the spermine to ceramide moiety through urethane group is postulated to induce electron withdrawal effect on the protons residing adjacent to the derivatized hydroxyl. The NMR analysis revealed that the H1a and H1b protons indeed were mostly affected and their peaks were shifted down field to δ=4.17 and 3.9 ppm respectively (in comparison to 5.36 ppm and 5.56 ppm in ceramide). H2 was slightly affected and shifted to δ=3.9 (δ=3.7 ppm at ceramide). In $^{13}$C-NMR, it was noticed that the C1 was shifted down field to δ=64.2 (δ=62.29 ppm at the starting material ceramide). The conjugation through HO(C1) caused only minor shifting on H3 and C3 (from δ=4.06 and 73.94 ppm at ceramide to δ=3.8 and 72.18 ppm at spermine-ceramide respectively).

In this case both the HO(C3) and amide were not detected apparently due to fast exchange with the deuterium from the solvent used.

TABLE 3

Spectral assignment of 1H NMR resonances for central region of spermine-ceramide conjugate in CD4O at 25° C. (see FIG. 8).

| Assignment | Chemical shift (ppm) |
|---|---|
| H1a | 1.17 |
| H1b | 3.9 |
| H2 | 3.9 |
| H3 | 4.8 |
| H4 | 6.32 |
| H5 | 5.6 |
| 2H2' | 2.88 |
| H—N | 6.474 |
| H—O(1) | Disappeared |
| H—O(3) | Broad signal |

TABLE 4

Spectral assignment of $^{13}$C NMR resonances for central region of spermine-ceramide conjugate in CD4O at 25° C. (see FIG. 8)

| Assignment | Chemical shift (ppm) |
|---|---|
| C1 | 64.2 |
| C2 | 63 |
| C3 | 72.1 |
| C4 | 133.9 |
| C5 | 136.3 |
| C1' | 174.87, 175.07 |
| C* | 178.07 |

Figure 9A:
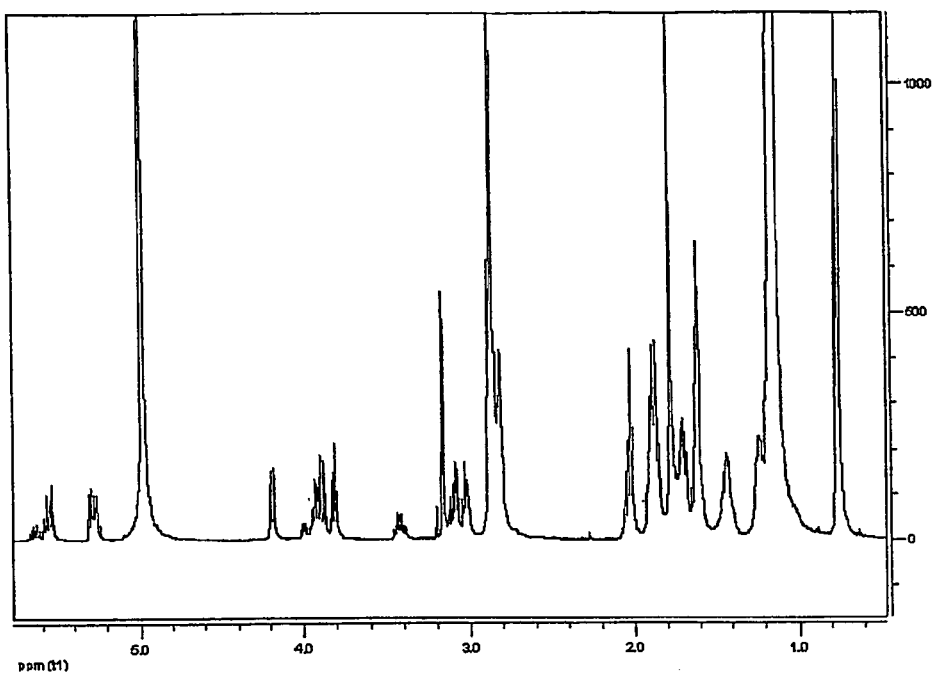
FIGS. 9A-9B present $^1$H-NMR (FIG. 9A) and $^{13}$C-NMR (FIG. 9B) of CCS as described below.
Figure 9B:
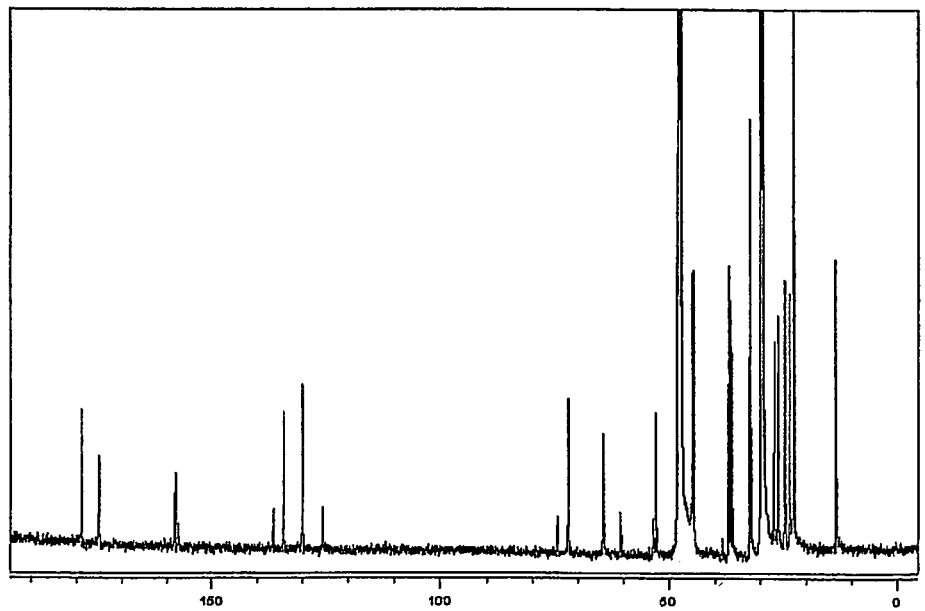

FIGS. 9A-9B present the 1H-NMR and 13C-NMR, respectively, of the CCS compound according to the invention, which correspond to the above results.

The invention will now be defined by the appended claims, the contents of which are to be read as included within the disclosure of the specification.

The invention claimed is:

1. A compound of formula (I):

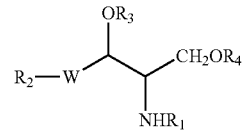

wherein
R$_1$ represents a hydrogen, a branched or linear alkyl, aryl, alkylamine, or a group —C(O)R$_5$;
R$_2$ and R$_5$ represent, independently, a branched or linear C$_{10}$-C$_{24}$ alkyl, alkenyl or polyenyl group;
R$_3$ and R$_4$ are, independently, a group —C(O)—NR$_6$R$_7$, in which R$_6$ and R$_7$, being the same or different for R$_3$ and R$_4$, represent, independently, a hydrogen, or a saturated or unsaturated branched or linear polyalkylamine, wherein one or more amine units in said polyalkylamine may be a quaternary ammonium; or R$_3$ is a hydrogen; or R$_3$ and R$_4$ form, together with the oxygen atoms to which they are bound, a heterocyclic ring comprising —C(O)—NR$_9$—[R$_8$—NR$_9$]$_m$—C(O)—, in which R$_8$ represents a saturated or unsaturated C$_1$-C$_4$ alkyl and R$_9$ represents a hydrogen or a polyalkylamine of the formula —[R$_8$—NR$_9$]$_n$—, wherein said R$_9$ or each alkylamine unit R$_8$NR$_9$ may be the same or different in said polyalkylamine; and n and m represent, independently, an integer from 1 to 10; and
W represents —CH=CH—, —CH$_2$—CH(OH)— or —CH$_2$—CH$_2$—.

2. The compound of claim 1, wherein R$_1$ represents a —C(O)R$_5$ group, R$_5$ being as defined.

3. The compound of claim 1, wherein said R$_2$ and R$_5$ represent, independently, a linear or branched C$_{12}$-C$_{18}$ alkyl or alkenyl group.

4. The compound of claim 1, wherein W represents CH=CH—.

5. The compound of claim 1, wherein R$_1$ represents a —C(O)R$_5$ group; R$_5$ represents a C$_{12}$-C$_{18}$ linear or branched alkyl or alkenyl; W represents —CH=CH—;
R$_2$ represents a C$_{12}$-C$_{18}$ linear or branched alkyl or alkenyl;
R$_3$ and R$_4$ represent, independently, a group —C(O)—NR$_6$R$_7$, and R$_3$ may also represent a hydrogen, wherein R$_6$ and R$_7$ represent, independently, a hydrogen or a polyalkylamine having the general formula (II):

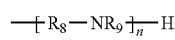

wherein
R$_8$ represent a C$_1$-C$_4$ alkyl;
R$_9$ represents a hydrogen or a polyalkylamine branch of formula (II), said R$_8$ and R$_9$ may be the same or different for each alkylamine unit, —R$_8$NR$_9$—, in the polyalkylamine of formula (II); and
n represents an integer from 3 to 6.

6. The compound of claim 5, wherein R$_3$ is a hydrogen atom.

7. The compound of claim 1, wherein R$_1$ represents a —C(O)R$_5$ group; R$_5$ represents a C$_{12}$-C$_{18}$ linear or branched alkyl or alkenyl; W represents —CH=CH—;
R$_2$ represents a C$_{12}$-C$_{18}$ linear or branched alkyl or alkenyl;
R$_3$ and R$_4$ represent, independently, a group —C(O)—NR$_6$R$_7$, wherein R$_6$ and R$_7$ represent, independently, an alkylamine or a polyalkylamine having the general formula (II):

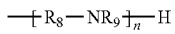

wherein
$R_8$ represents a $C_1$-$C_4$ alkyl;
$R_9$ represents a hydrogen or a polyalkylamine branch of formula (II), said $R_8$ and $R_9$ may be the same or different for each alkylamine unit, —$R_8NR_9$—, in the polyalkylamine of formula (II); and
n represents an integer from 3 to 6.

8. The compound of claim 1, wherein $R_1$ represents a —C(O)$R_5$ group; $R_5$ represents a $C_{12}$-$C_{18}$ linear or branched alkyl or alkenyl; W represents —CH=CH—;
$R_2$ represents a $C_{12}$-$C_{18}$ linear or branched alkyl or alkenyl;
$R_3$ and $R_4$ form, together with the oxygen atoms to which they are bonded, a heterocyclic ring comprising —C(O)—[NH—$R_8$]—NH—C(O)—,
wherein
$R_8$ represents a $C_1$-$C_4$ alkyl, wherein for each alkylamine unit having the formula —NH—$R_8$—, said $R_8$ may be the same or different; and
n represents an integer from 3 to 6.

9. The compound of claim 1, wherein said $R_8$ is a $C_3$-$C_4$ alkyl.

10. The compound of claim 1, being N-palmitoyl D-erythro sphingosyl-1-carbamoyl spermine.

11. A process for the preparation of a sphingoid-polyalkylamine conjugate of formula (I)

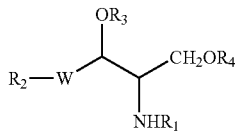

wherein
$R_1$ represents a hydrogen, a branched or linear alkyl, aryl, alkylamine, or a group —C(O)$R_5$;
$R_2$ and $R_5$ represent, independently, a branched or linear $C_{10}$-$C_{24}$ alkyl, alkenyl or polyenyl group;
$R_3$ and $R_4$ are, independently, a group —C(O)—NR$_6$R$_7$, in which $R_6$ and $R_7$, being the same or different for $R_3$ and $R_4$, represent, independently, a hydrogen or a saturated or unsaturated branched or linear polyalkylamine, wherein one or more amine units in said polyalkylamine may be a quaternary ammonium; or $R_3$ and $R_4$ form together with the oxygen atoms to which they are bound a heterocyclic ring comprising —C(O)—NR$_9$—[$R_8$—NR$_9$]$_m$—C(O)—, in which $R_8$ represents a saturated or unsaturated $C_1$-$C_4$ alkyl and $R_9$ represents a hydrogen or a polyalkylamine of the formula —[$R_8$—NR$_9$]$_n$—, wherein said $R_9$ or each alkylamine unit $R_8NR_9$ may be the same or different in said polyalkylamine; and n and m represent, independently, an integer from 1 to 10; and
W represents —CH=CH—, —CH$_2$—CH(OH)— or —CH$_2$—CH$_2$—;
the process comprising:
(a) providing a sphingoid compound of formula (I) wherein $R_1$, $R_2$ and W have the meaning as defined above and $R_3$ and $R_4$ represent, independently, a hydrogen atom or an oxo protecting group, wherein at least one of said $R_3$ and $R_4$ represent a hydrogen atom;
(b) reacting said compound of step (a) with an agent for activating the hydroxyl moieties of OR$_3$ and/or OR$_4$, said activating agent being selected from the group consisting of N,N'-disuccinimidylcarbonate, di- or tri-phosgene and an imidazole derivative, optionally in the presence of a catalyst, to obtain an activated OR$_3$ and/or OR$_4$ group;
(c) reacting said activated sphingoid compound with a polyalkylamine; and
(d) removing said protecting group, thereby obtaining said sphingoid-polyalkylamine conjugate of formula (I) as defined above.

12. The process of claim 11, wherein said sphingoid-polyalkylamine conjugate is N-palmitoyl D-erythro sphingosyl-1-carbamoyl spermine.

13. The process of claim 11, wherein said protecting group is a primary amine protecting group selected from the group consisting of trifluoroacetamide, fmoc, carbobenzoxy (CBZ), and dialkyl phosphoramidates.

14. The process of claim 11, wherein said activation is performed in the presence of a catalyst, the catalyst being 4-dimethylamino pyridine (DMAP), tetrazole, dicyanoimidazole or diisopropylethylamine.

15. The process of claim 11, for obtaining a di-substituted sphingoid-polyalkylamine conjugate, wherein
in step (a) both $R_3$ and $R_4$ are hydrogen atoms, and said process comprises reacting the compound of formula (I) with at least two equivalents of polyalkylamine to obtain a disubstituted sphingoid-polyalkylamine conjugate, with identical polyalkylamine substituents.

16. The process of claim 11, for obtaining a di-substituted sphingoid-polyalkylamine conjugate, wherein
in step (a) at least one of $R_3$ or $R_4$ is protected with a protecting group, the process comprises reacting in step (c) the activated sphingoid compound with a first polyalkylamine;
removing the protecting group of $R_3$ or $R_4$ to obtain an unprotected oxo group; reacting the unprotected compound with a said activating agent to obtain an activated mono-substituted sphingoid-polyalkylamine conjugate; and reacting said activated mono-substituted sphingoid-polyalkylamine conjugate with a second polyalkylamine, thereby obtaining a di-substituted sphingoid-polyalkylamine conjugate, in which said first and second polyalkylamine may be the same or different.

17. The process of claim 11, for obtaining any one of the sphingoid-polyalkylamine conjugates as follows:

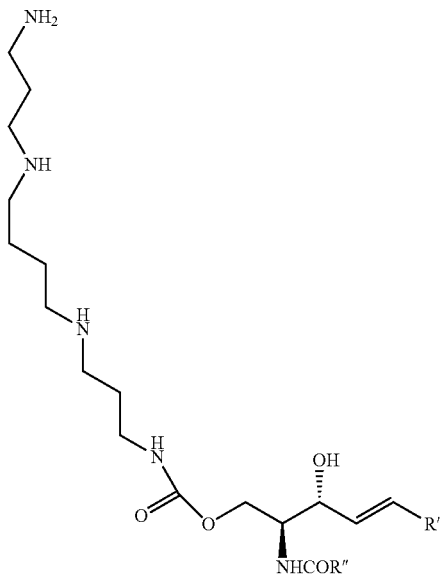

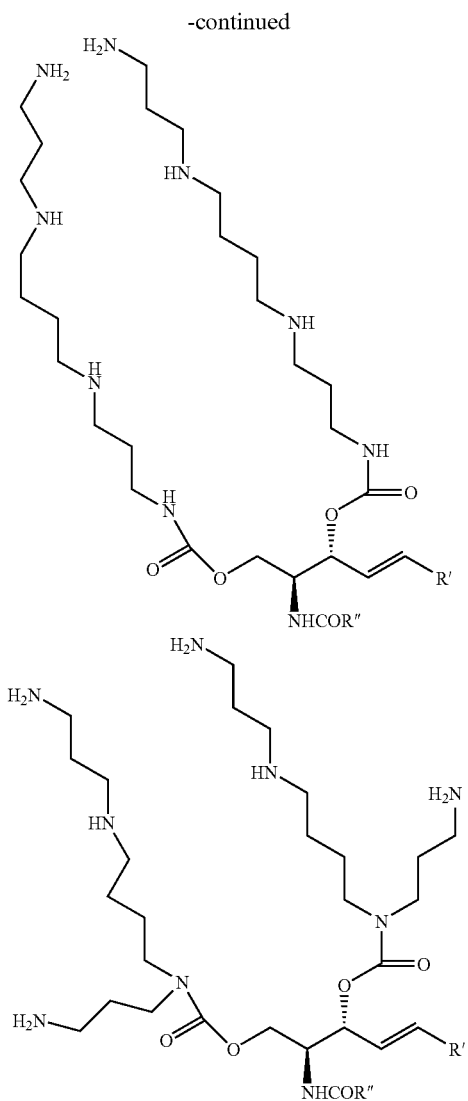

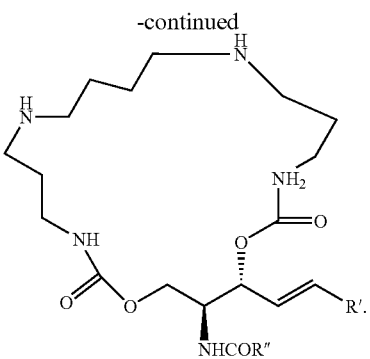

18. The process of claim 11, for obtaining a heterocyclic sphingoid-polyalkylamine conjugate, wherein
in step (a) both $R_3$ and $R_4$ are hydrogen atoms, said sphingoid compound is reacted with at least two equivalents of a said activating agent to obtain an activated sphingoid with both $R_3$ and $R_4$ activated and reacting said activated sphingoid compound with less than an equivalent of polyalkylamine, thereby obtaining a heterocyclic sphingoid-polyalkylamine conjugate.

19. A composition comprising a sphingoid-polyalkylamine conjugate in accordance with claim 1, and a pharmaceutically acceptable carrier.

20. The composition of claim 19, wherein said sphingoid-polyalkylamine conjugate is N-palmitoyl D-erythro sphingosyl-1-carbamoyl spermine.

21. The composition of claim 19, further comprising a biologically active molecule.

22. In the method of capturing a molecule having a negative charge, a negative dipole or a local negative dipole with a conjugate capable of capturing said molecule by electrostatic interaction, the improvement wherein said conjugate is a compound in accordance with claim 1.

23. The method of claim 22, wherein said compound is N-palmitoyl D-erythro sphingosyl-1-carbamoyl spermine.

24. The compound of claim 5, wherein $R_3$ and $R_4$ represent the same or different polyalkylamine.

* * * * *